United States Patent
Freiman et al.

(10) Patent No.: US 12,310,774 B2
(45) Date of Patent: May 27, 2025

(54) DEEP SPECTRAL BOLUS TRACKING

(71) Applicant: KONINKLIJKE PHILIPS N.V., Eindhoven (NL)

(72) Inventors: Mordechay Pinchas Freiman, Zichron-Yaakov (IL); Liran Goshen, Pardes-Hanna (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 762 days.

(21) Appl. No.: 17/290,849

(22) PCT Filed: Nov. 5, 2019

(86) PCT No.: PCT/EP2019/080156
§ 371 (c)(1),
(2) Date: May 3, 2021

(87) PCT Pub. No.: WO2020/094596
PCT Pub. Date: May 14, 2020

(65) Prior Publication Data
US 2021/0386389 A1    Dec. 16, 2021

(30) Foreign Application Priority Data
Nov. 7, 2018   (EP) .................................. 18204885

(51) Int. Cl.
*A61B 6/00*    (2024.01)
*A61B 6/46*    (2024.01)
(Continued)

(52) U.S. Cl.
CPC .............. *A61B 6/481* (2013.01); *A61B 6/461* (2013.01); *A61B 6/467* (2013.01); *A61B 6/504* (2013.01);
(Continued)

(58) Field of Classification Search
CPC ......... A61B 6/481; A61B 6/461; A61B 6/467; A61B 6/504; A61B 6/508; A61B 6/54; G06N 3/04; G06N 3/08
See application file for complete search history.

(56) References Cited

U.S. PATENT DOCUMENTS 4,445,226 A    4/1984   Brody
7,606,614 B2   10/2009  Licato
(Continued)

FOREIGN PATENT DOCUMENTS

CN    107516330 A    12/2017
JP    2018089301 A    6/2018
WO    WO20120093364 A1   7/2012

OTHER PUBLICATIONS

PCT International Search Report, International application No. PCT/EP2019/080156, Feb. 4, 2020.
(Continued)

*Primary Examiner* — Sean A Frith
(74) *Attorney, Agent, or Firm* — Larry Liberchuk

(57) ABSTRACT

A computer-implemented system for supporting an imaging operation and related methods. The system comprises one or more input interfaces (IN) for receiving input data including an input image procured by an imaging apparatus (IA) of a target location (ROI) in a conduit (VS) of an object (OB). The conduit includes a target substance (CA) and the target substance (CA) is propagatabale in the conduit towards the target location. A pretrained-machine learning component (MLC2) is configured to process the input data to obtain output data indicative of an arrival of the said target substance at said target location. An output interface (OUT) outputs said output data.

9 Claims, 10 Drawing Sheets

(51) Int. Cl.
    *A61B 6/50*     (2024.01)
    *G06N 3/04*     (2023.01)
    *G06N 3/08*     (2023.01)

(52) U.S. Cl.
    CPC ............... *A61B 6/508* (2013.01); *A61B 6/54* (2013.01); *G06N 3/04* (2013.01); *G06N 3/08* (2013.01)

(56) References Cited

U.S. PATENT DOCUMENTS

| | | | |
|---|---|---|---|
| 9,047,702 B2 | 6/2015 | Schmitt | |
| 9,414,798 B2 | 8/2016 | Feuerlein | |
| 9,730,643 B2 | 8/2017 | Georgescu | |
| 10,438,380 B2 | 10/2019 | Hu | |
| 11,020,081 B2 | 6/2021 | Korporaal | |
| 2008/0292049 A1* | 11/2008 | Camus | A61B 6/504 378/21 |
| 2011/0002520 A1* | 1/2011 | Suehling | G06T 7/0012 382/154 |
| 2012/0236995 A1 | 9/2012 | Eusemann | |
| 2013/0308847 A1 | 11/2013 | Schirra | |
| 2017/0147782 A1* | 5/2017 | Haberland | G16H 30/20 |
| 2017/0258412 A1* | 9/2017 | Daerr | A61B 6/4241 |
| 2018/0018757 A1 | 1/2018 | Suzuki | |
| 2018/0025256 A1* | 1/2018 | Bai | G06F 18/2415 382/229 |
| 2018/0071452 A1* | 3/2018 | Sharma | A61M 5/007 |
| 2018/0254098 A1 | 9/2018 | Allmendinger | |
| 2018/0368781 A1* | 12/2018 | De Man | A61B 5/055 |

OTHER PUBLICATIONS

Panta R. K. et al., "Element Specific Spectral Imaging of Multiple Contrast Agents: A Phantom Study", Feb. 6, 2018, Journal of Instrumentaion (JINST).

Bai E-W. et al., "An Adaptive Optimal Control Design for a Bolus Chasing Computed Tomography Angiography", IEEE Transactions on Control Systems Technology, vol. 16, No. 1, pp. 60-69, Jan. 2008.

Mehnert F. et al., "Biphasic Spiral CT of the Liver: Automatic Bolus Tracking or Time Delay?," Eur. Radiol., vol. 11, No. 3, pp. 427-431, 2001.

Birnbaum B. A. et al., "Assessment of a Bolus-Tracking Technique in Helical Renal CT to Optimize Nephrographic Phase Imaging," Radiology, vol. 211, No. 1, pp. 87-94, 1999.

Cademartiri F. et al., "Intravenous Contrast Material Administration at 16-Detector Row Helical CT Coronary Angiography: Test Bolus versus Bolus-tracking Technique", Radiology, vol. 233, No. 3, pp. 817-823, 2004.

Danad I. et al., "Dual-Energy Computed Tomography for Detection of Coronary Artery Disease.," Expert Review of Cardiovascular Therapy, vol. 13, No. 12, pp. 1345-1356, 2015.

Mitchell T. M. et al., "Machine Learning", p. 2, section 1.1, McGraw-Hill, 1997.

Zeiler M. D. et al., "Adaptive Deconvolutional Networks for Mid and High Level Feature Learning", 2011 International Conference on Computer Vision.

Ronneberger O. et al., "U-Net: Convolutional Networks for Biomedical Image Segmentation", Medical Image Computing and Computer-Assisted Intervention—MICCAI, 2015. Lecture Notes in Computer Science, Springer, vol. 9351, pp. 234-241.

Choy G. et al., "Current Applications and Future Impact of Machine Learning in Radiology", Radiology, vol. 288, No. 2, Aug. 1, 2018 (Aug. 1, 2018), pp. 318-328, XP055661344.

\* cited by examiner

DEEP SPECTRAL BOLUS TRACKING

FIELD OF THE INVENTION

The invention relates to systems for image processing, to systems for training machine learning components for image processing, to methods for image processing, to methods for training machine learning components for image processing, to a computer program element, and to a computer readable medium.

BACKGROUND OF THE INVENTION

Computed tomography angiography (CTA) is a computed tomography based imaging technique used to visualize arterial and venous vessels throughout the body.

Examples include: arteries supplying blood to the brain, coronary arteries supplying blood to the cardiac muscle, among others. The CTA images are produced by acquiring the CT data after injecting contrast agents into the bloodstream.

A prerequisite for successful CT angiography is good, if not optimal, synchronization between the arterial passage of contrast material and CT data acquisition.

Several approaches were proposed for determining the time of arrival at an organ of inflowing contrast agent injected into a peripheral vein:
1) A fixed delay technique in which the CT scan is started in a fixed delay after the contrast injection. This may yield suboptimal result owing different blood flow rates for different patients
2) Determining the transit time by using a test bolus injection. This result in multiple scans and a larger amount of contrast material administrated to the patient.
3) Bolus tracking. In this approach a thin image slab is acquired and updated regularly using multiple short scans. The image intensity in a user-defined area is monitored, and the diagnostic image acquisition is started when a pre-defined intensity value is reached, indicating that the bolus has arrived at the target region.

However, bolus tracking approach to synchronize the CT scan with the contrast material flow has several shortcomings, including: a) significant amount of X-ray dose that is spent only to find out the correct starting time of the acquisition, b) sufficient amount of contrast material administrated to the patient so that the intensity enhancement will be visible to the user/automatic algorithm triggering the CT acquisition, c) subjectively ROI selection and thresholds setting by various users to trigger the acquisition may result in variable image quality.

SUMMARY OF THE INVENTION

There may therefore be a need for alternative systems or methods to support image-based analysis, in particular, but not only, in bolus tracking.

The object of the present invention is solved by the subject matter of the independent claims where further embodiments are incorporated in the dependent claims. It should be noted that the following described aspect of the invention equally applies to the computer program element and to the computer readable medium.

According to a first aspect of the invention there is provided a (computer-implemented) system for image processing, comprising:

one or more input interfaces for receiving input data including an input image, procured through an imaging apparatus, of a target location ("ROI") in a conduit of an object the conduit including a target substance, the target substance propagatabale in the conduit towards said target location;

a pre-trained-machine learning component configured to process the input data to obtain output data indicative of an arrival of the said target substance at said target location; and an output interface for outputting said output data. The output data may indicate for instance the mass or concentration of the substance at the location. The output data may be used for training purposes. Preferably, in embodiments, the system includes an imaging control component configured to control operation of the imaging apparatus based on the output data. Specifically, in embodiments, the imaging control component is configured to trigger an image acquisition operation. In this embodiment, the output may include a trigger schedule or instructions such as "1" for "start imaging" or "0" or "hold".

Preferably, input image forms "live" image of the location of interest, procured in a monitoring operation. Preferably, a series of such input images are acquired as a live feed to monitor the location for the arrival of the substance, such as a bolus of contrast material in medical imaging. In short, the one or more input images are preferably procured in the context of a live bolus tracking session. The "object", may be a patient and the input images are procured in relation to this patient.

In embodiments, the image acquisition operation so triggered includes acquiring a plurality of projection images from different directions relative to the target location. In other words, an actual, that is diagnostic imaging, is triggered for specific patient In CT, preferably as full scan is so triggered, with rotation of, for instance, about 180°. The triggered imaging operation is preferably for diagnostic purposes and may be done at higher dose than the dose that was used for to acquire the input image(s) during the monitoring.

In embodiments, the machine learning component is arranged as a neural network, in particular as a convolutional neural network.

In embodiments, the neural network has a depth of at least one, better two or more. In particular, the neural network includes at least one hidden layer, preferably two or more hidden layers. In embodiments, the neural network includes at least two hidden layers, wherein at least one hidden layer causes a reduction of data dimension and the at least one other hidden layer of the at least two layers causes an increase in data dimension. This implements an up- and down sampling which helps achieve more robust performance as overfitting can be kept contained. Also, using a deep architecture, allows multi-scale analysis of the input imagery, thus enhancing the ratio of correct performance even more.

In embodiments, the input image procured by the or another imaging apparatus is configured for spectral imaging. Specifically, the input image may be processed by a spectral imaging algorithm to better adapt same to the contrast agent material.

In embodiments, the conduit includes at least a part of a human or animal vessel holding or conveying body fluid. In one embodiments the conduit is a vessel, such as coronaries (artery or vein) of a human or animal (e.g., mammal) heart. In embodiments, wherein the target substance includes contrast agent for medical imaging. However, non-medical contexts are also envisaged herein.

In embodiments, the procured input image is at least one projection image acquired by the imaging apparatus. Preferably, a single projection image is acquired by the imaging apparatus at a time during the monitoring is acquired at a suitable sampling frequency. The direction from which the input projection images are acquired during the monitoring may remain constant or may change.

The imaging apparatus used for acquiring the projection image(s) during the monitoring is preferably the same as the one used for the triggered diagnostic imaging, but in embodiments the two may differ, so two imaging apparatus, of the same or different modalities, may also be envisaged herein. Preferably but necessarily, the diagnostic imaging is done at a higher dose than the monitoring imaging.

In embodiments, the input data includes any or more of the following: i) data that describes the object, ii) data that describe a manner of propagation of the substance. This data forms contextual data, which may include non-image data. It allows achieving better performance, such as better robustness, of the machine learning component.

In embodiments, the target location is previously identified by a further machine learning component based on at least an imaging protocol used by the imaging apparatus. In other words, in this embodiment there are two machine-learning algorithms, one to predict tracking parameters and one to start the scan based on actual tracking data as mentioned above.

In another aspect there is provided a method of supporting an imaging operation, comprising:
  receiving input data including an input image, procured through an imaging apparatus, of a target location in a conduit of an object, the conduit including a target substance, the target substance propagatabale in the conduit towards said target location;
  processing, by way of a pre-trained-machine learning component, the input image to obtain output data indicative of an arrival of the of said target substance at said target location; and
  outputting said output data.

The proposed system or method herein is of particular benefit in angiographic applications where the bolus of contrast agent is administered to a patient. Applications in other than x-ray based imaging such as MRI, PE, SPECT or others are also envisaged herein and imaging scenarios include cardiac imaging and others. The proposed method, in particular, the combination of deep learning based machine learning architectures and the use of spectral imagery allows accurate bolus tracking, particularly for CT angiography, even when low doses of contrast materials are used. Another benefit of the invention resides in its ability to use for the monitoring imaging merely projection imagery rather than re-constructed imagery. As mentioned above, in embodiments, a single projection image at a time during the monitoring may be used. Being able to use as few as a single projection image at a time for accurate bolus tracking may be due to using spectral imagery and/or having the machine learning component configured in particular in a deep learning architecture. Such deep learning architectures include, but are not limited to, neural networks, in particular at least portions of a convolutional neural network (CNN), with at least one, better two, or more than two hidden layers.

In embodiments, the proposed methods and systems enable improved, accurate, objective and standardized CT scan synchronization with the contrast material administration using deep learning based spectral bolus tracking. The proposed systems and methods preferably utilizes spectral CT or radiography data along with deep-learning based modules to automatically perform any one or more of i) locate the ROI, ii) track the bolus and iiii) trigger an image acquisition operation, such as full CT, MRI or PET/SPECT scan.

The ability to track bolus of a reduced amount of contrast material has the potential to reduce adverse side effects associated with currently used contrast agent dosage and to still achieve a better and more standardized, consistent image quality in particular in CTA scans.

Further aspects envisaged herein include a system for supporting an imaging operation, comprising:
  one or more input interfaces for receiving input data including a specification of an imaging operation and/or data that describes an object to be imaged;
  a pre-trained-machine learning component configured to process the input data to obtain output data indicative of i) a target location within an object and/or ii) of a manner of propagation of a target substance propagatabale through a conduit of the object towards the target location; and
  an output interface for outputting said output data.

In embodiments, any one or more of the above mentioned system is fully or at least in parts integrated into the imaging apparatus.

In another aspect there is provided a method of supporting an imaging operation, comprising:
  receiving input data including a specification of an imaging operation and/or data that describes an object to be imaged;
  processing, by way of a pre-trained-machine learning component, the input data to obtain output data indicative of i) a target location within an object and/or ii) of a manner of propagation of a target substance propagatabale through a conduit of the object towards the target location; and
  outputting said output data.

In another aspect there is provided a system configured to train any one of the above mentioned machine learning components.

In another aspect there is provided a method for training a machine learning component as used in any one aspects or embodiments. The learning method may include:
  providing training data;
  applying the training data to a model for the respective learning component; and
  running a training algorithm to adjust one or more parameters of the model to effect the learning. The steps may iterative over items of training data.

In another aspect there is provided at least one computer program element, which, when being executed by at least one processing unit, is adapted to cause the processing unit to perform a method as per any one the above mentioned aspects.

Preferably the processing unit is of a multi-core design and/or configured for parallel computing.

In another aspect there is provided at least one computer readable medium having stored thereon the program element.

Training and deployment can be done on the same computing hardware, or may be done on different hardware arrangements.

"Procuring" as used above includes acquiring image data in the projection domain by operation of an imaging apparatus, but also includes forming, in particular through reconstruction, from such projection data, image data in the image domain.

A "configuration" as used herein comprises all model parameters (weights, filter coefficients) that are adjustable during training. A given set of such variable defines the way an MLC acts, thus forms a configuration of the MLC.

In general, the "machine learning component" is a computerized arrangement that implements a machine learning ("ML") algorithm that is configured to perform a task. In an ML algorithm, task performance improves measurably after having provided the arrangement with more training data TI. The task's performance may be measured by objective tests when feeding the system with test data. The task's performance may be defined as requiring a certain error rate to be achieved for the given test data. See T. M. Mitchell, "*Machine Learning*", page 2, section 1.1, McGraw-Hill, 1997.

BRIEF DESCRIPTION OF THE DRAWINGS

Exemplary embodiments of the invention will now be described with reference to the following drawings which are not to scale, wherein.

DETAILED DESCRIPTION OF EMBODIMENTS

Figure 1:
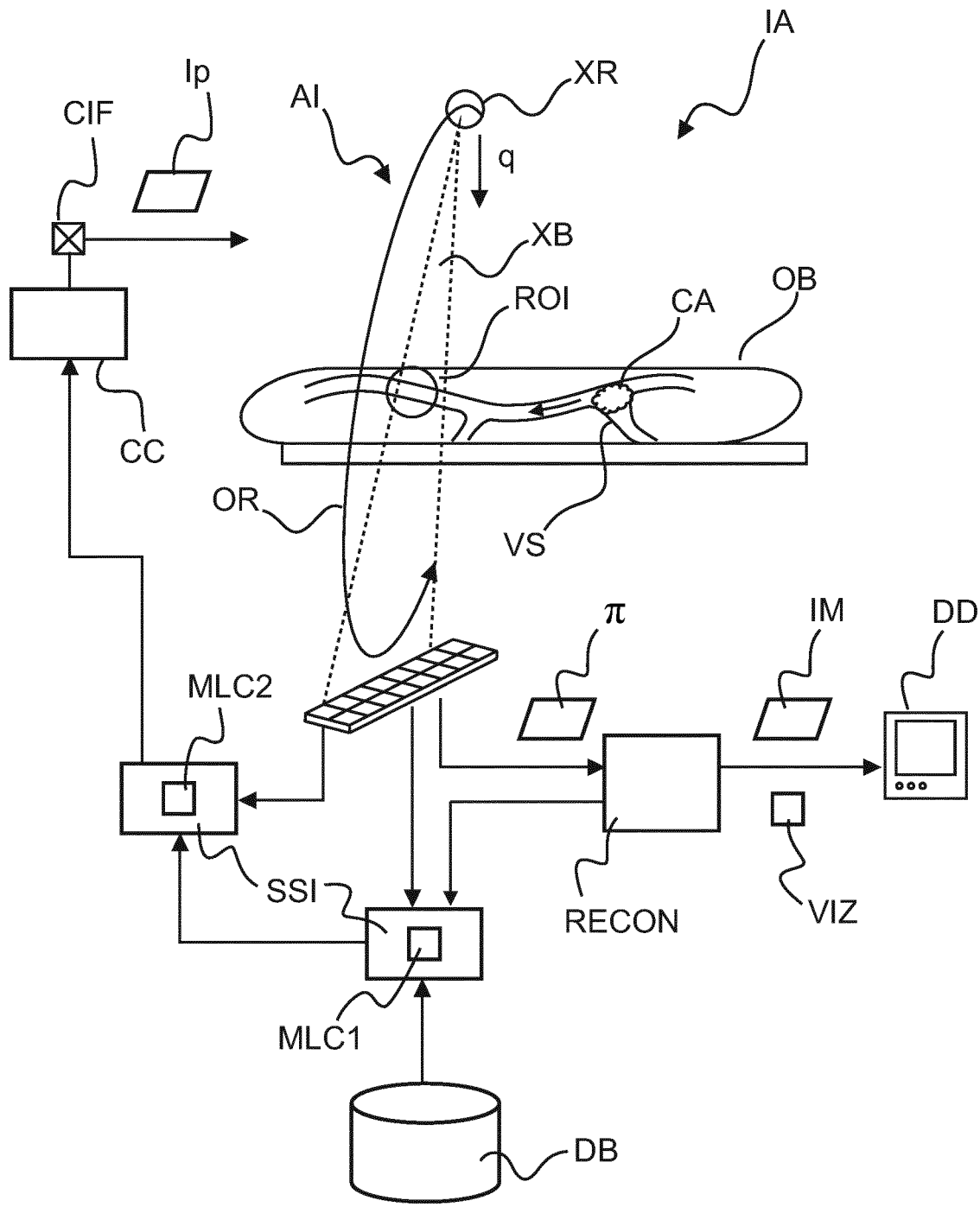
FIG. 1 shows a schematic block diagram of an imaging arrangement.

With reference to the schematic block diagram of FIG. 1 there is shown a schematic block diagram of an imaging arrangement. The imaging arrangement may include an imaging apparatus IA and a computerized system SSI (also referred to herein as the "SSI") to support imaging, in particular to support imaging by the imaging apparatus AI or other imaging apparatuses.

The imaging apparatus IA is preferably but not necessarily x-ray based and is configured to acquire one or more images of an object OB.

The SSI is configured to support the imaging operation by analyzing data in relation to the object. The data may include the (one or more) images that are acquired by the imaging apparatus of the object OB or imagery that are derivable from the images so acquired. The SSI is preferably a computerized system.

Although main applications for the imaging arrangement envisaged herein are in the medical field, non-medical contexts such as non-destructive material testing or baggage screening, etc. are not excluded herein. Accordingly, the term "object OB" is used herein in the general sense to include animate "objects" such as a human or animal patient, or anatomic parts thereof but also includes inanimate objects. However, proposed system SSI will be discussed herein with main reference to the medical field, so we will be referring to the object OB as "the patient" and the location of interest ROI, being a particular anatomy or group of anatomies of the patient OB.

The SSI includes one or two of the following components: a machine learning component MLC2 that is configured to analyze imagery of the object and to then based, on the analysis, control operation of the imaging apparatus. The machine learning component MLC2 may be used to benefit in application scenarios where a certain location of interest in the object that needs to be examined and when the said location is inaccessible, occluded or otherwise embedded in surrounding non-transparent material thus evading direct visual inspection.

One such application scenario envisaged herein is the image based examination of internal locations in conduits VS where a substance CA is used to enhance contrast in imagery of the location ROI acquired by the imaging apparatus. A preferred application scenario and embodiment mainly envisaged herein is in the medical field, namely in x-ray based imaging, in particular angiography. Angiography may be based on 2D imagery such as in radiography or on 3D imagery, such as CT scanner based angiography (CTA) or in other rotational imaging applications, such as in C-arm imaging. Although in the following main reference will be made to x-ray based imaging, the proposed system may also be used in benefit of other imaging modalities such as contrast agent use in MRI imaging or others.

In x-ray based angiography, a bolus is administered to the patient OB through a suitable entry point such as in the femoral vein or artery. The patient OB may reside on a support T during the angiography procedure. The bolus is a defined amount of a substance, a contrast agent CA, that is administered to enhance contrast in particular in soft tissue imagery. Suitable contrast materials include Iodine-based for CT or Gadolinium based for MRI. Orally administered contrast agents, such as Barium-Sulfate, are also envisaged. After administration, the bolus propagates with the blood flow from an entry point to the target location. After a certain amount of time, the transit time, some or all of the substance CA reaches the intended target location and passes this location. The target location may be a particular type of vessel VS such as the coronaries of the patient's OB heart. To maximize the benefits of angiographic imaging, diagnostic images should be acquired just at the right time when a sufficient amount of contrast agent arrives and accumulates at the target location. If the image acquisition is triggered too early, before enough contrast agent has accumulated, image contrast may be poor. But if image acquisition is triggered too late, image contrast will be likewise poor as the contrast agent may have already passed the target location. In this or similar applications as mainly envisaged herein, bolus tracking procedure is used. In bolus tracking, the target location is monitored by acquiring one or more monitoring images, in other words real time live images of the location of interest (also referred to herein as the region of interest ROI), that are analyzed by the machine learning component MLC2 to establish the point in time (referred to herein as the "trigger time") when sufficient contrast agent has arrived at the location and to then effect the diagnostic imaging acquisition. The machine learning component implements a decision logic to decide when to trigger the diagnostic image acquisition. For the diagnostic imaging a higher dose is generally used than for acquiring the monitoring imaging to reduce x-ray dose exposure to the patient.

The trigger time will be understood to be function of many factors such as physical characteristics of the patient, the state of the vessel lumen, the viscosity of the blood, the blood flow rate, the contrast agent type used. These factors can be expected to have a bearing on how the initially administered bolus disperses, mixes and propagates with the surrounding fluid, e.g., with the blood. These factors combine to impart how the shape of the bolus changes during transit time. The bolus will have, for different patients OB, different appearances as it passes through the location of interest. There is a functional relationship between the appearance of the bolus (or at least a part thereof) that eventually presents at the location of interest and the trigger time. And the bolus appearance in turn will determine the intensity pattern recordable by the monitoring images, which are preferably in the projection domain, at the location of interest. There is hence a mapping between the contrast distribution (or intensity pattern) recordable at the location of interest and the trigger time. As such, this mapping, called the underlying mapping, is unknown and can be expected to be relatively complex. The machine learning component MLC2 as envisaged herein is configured to learn from historical training data the underlying mapping to sufficient approximation and to then estimate the trigger time for future angiographic applications. Such an embodiment of the learning component MLC2 may be referred to in the following as the "bolus tracker". It will be understood however that the machine learning component MLC2 may also be used to control imaging operations other than image acquisition triggering, such as any one or more of stopping an active image acquisition, change acquisition mode (high energy/low energy).

In addition to the bolus tracker embodiment MLC2 or instead thereof, the support system SSI may include another machine learning component MLC1 that is configured to establish spatially the above mentioned target location based on suitable input data, including the imaging protocol data. This input data may or may not include image data. In addition or instead, the machine learning component MLC2 may be configured to establish suitable bolus tracking parameters (also referred to herein as "BTP") that may be used as input for the bolus tracker MLC2. This second embodiment MLC1 of the machine learning component may be referred to herein as the "context finder".

It will be understood however, that the context finder may be configured as a stand-alone application and is not necessarily tied to the bolus tracker. Equally, the bolus tracker may be used as standalone application without the context finder. Advantageously, both, the bolus tracker MLC1 and the context finder MLC2 may be used in combination as envisaged in embodiment. Furthermore, it will be understood that the bolus tracker and the context finder may be used for medical applications other than bolus tracking. Even non-medical applications are envisaged where image-based examination of concealed locations in a conduit is called for. This may include hydrology, for instance examination of water flow in subterranean cave systems, or leakage detection in plumbing systems.

Before describing the two machine learning embodiments, the bolus tracker MLC2 and the context finder MLC1 in further detail, the following terminology may be useful in the context of, in particular, bolus tracking applications.

The term "bolus" as used herein may relate to an amount of substance that is administered to the object of interest such as the human or animal patient with a purpose to increase image contrast at a desired target location also referred to as the region of interest ROI. The point of administration of the contrast agent is in general different from the location of interest. There is in general a transit time for the contrast agent substance to travel from the point of administration to the location of interest.

The term "bolus tracking parameters (BTP)" used herein refers to parameters that are capable to describe the propagation of the bolus and/or that can be used to define a nature of the bolus at different locations, in particular at the location of interest. More particularly, the bolus tracking parameters are suitable to establish the trigger time.

The procedure of "bolus tracking" as mainly envisaged herein in x-ray based embodiments relates to inferring the presence of some or all of the administered bolus at the target location based on a particular, but not necessarily, an image acquired at the target location or image data derivable from imagery so acquired.

With continued reference to FIG. 1, the above described components of the imaging arrangement are now described in more detail. Turning now first to the imaging apparatus, this in general includes a component capable of generating an interrogating signal and a sensor component to detect the interrogating signal after interaction of this interrogating signal with the patient OB, in particular with the location of interest ROI.

Examples for the imaging apparatus envisaged herein include x-ray imaging apparatuses. An x-ray apparatus is configured to acquire an x-ray image of the patient OB. In the case of x-ray imaging the interrogating signal is x-ray radiation and the above-mentioned component is the x-ray source XR. Correspondingly in x-ray imaging the sensor is an x-ray detector D. Embodiments of x-ray imaging apparatuses envisaged herein include a C-arm imaging apparatus, a CBCT (Cone Beam CT) scanner, a CT scanner, a spectral CT scanner, a mammography apparatus or a radiography apparatus, or other, each configured to acquire an X-ray image of an object PAT.

In more detail, the X-ray imaging apparatus IA includes an X-ray source XS and an X-ray sensitive detector XD. In use, the patient OB is positioned along axis z in an examination region within the X-ray source XS and the X-ray detector XD. The X-ray source XS is energized to produce an X-ray beam XB which emanates from a focal spot FS and traverses the examination region and hence at least a region of interest of the object OB. The X-radiation beam XB interacts with matter (e.g. tissue, bones, etc.) of the object OB. After interaction, the X-radiation emerges at the far side of the object OB to then impinge on the X-ray detector XD. The impinging X-radiation is detected by the detector XD and converted into electrical signals. The electrical signals are converted by suitable conversion circuitry (not shown) into a collection of image values which form an image, in this case an X-ray projection image. The X-ray images are capable of revealing details of internals anatomies of the imaged patient OB. This can help in diagnosis and therapy or other examination of the imaged patient OB. The images may include projection imagery. In addition to X-ray imaging where attenuation is the main contrast mechanism, other variants such as phase contrast imaging or dark-field imaging, are also envisaged herein.

In rotational 3D imaging, as set of projection images is collected from different directions q during a rotation by the X-ray source XR along an orbit OR around the ROI. The orbit is in general an arc of up to 180°. The projection imagery supplied by the rotational X-ray imager IA may be further processed into axial or slice imagery IM by a processor RECON that implements a tomographic reconstruction algorithm, such as Radon transform based algorithms, including filtered backprojection (FBP), ART, iterative reconstructions, Fourier domain based reconstruction, but also machine learning based reconstructions. The reconstruction algorithm converts the projection imagery from 2D in the detector domain into the slice or axial imagery of a 3D volume in an image domain. The image domain is situated in the examination region and passes through the object PAT. Thus, a CT 3D volume may be obtained that is made up of a collection or "stack" of such 2D slice images, one for each position on the imaging axis z.

In other envisaged imaging modalities such as MRI, SPECR, PET, other reconstruction algorithms may be used that convert signals from the detector domain into the respective image domain (that is, a part of space where the object to be imaged is situated).

The image values in the projection or reconstructed images may be organized in a suitable data structure, such as one or more n-dimensional matrices, or "tensors" (n>3). Suitable values for n are 1, 2, 3, 4 or n>4. The image may be greyscale or color. Color imagery may be encoded in an RGB scheme or another suitable encoding scheme. For instance, the image values may be represented in rows and columns i,j to represent spatially two dimensional structures. Spatially three dimensional image values may be represented as rows and columns i,j and a depth component k.

In embodiments the image may be represented in a 2D structure with rows and columns i,j but the image in fact forms a section or sub-space of a three dimensional volume such as the slice imagers of a CT 3D volume. Similarly, MRI volumes may also include 2D slice images which are sections in 3D. 2D or 3D imagery acquired through time may be represented as a 3D or 4D image data, respectively, with the third or fourth component representing acquisition time.

Even though the imagery represents 2D structures, at times a higher dimensional representation may still be used such as in color images encoded in RGB. An RGB image may be represented as a three dimensional structure with the two spatial dimensions i,j corresponding whilst another component represents the red, green and blue image values respectively for any given image location i,j. In other words, 2D color image maybe represented as a 3D volume formed by the super position of three distinct 2D images each representing respectively the red, green and blue image values for a given image location. Accordingly, spatially 3D color imagery acquired through time may thus be represented as a seven-dimensional tensor: three spatial dimensions, three dimensions for the color values, and one dimension for time. A grey value image may be represented without an additional depth component.

When obtaining the imagery using the imaging apparatus IA, one or more acquisition parameters AP may need to be adjusted by an imaging control unit CC that controls the imaging operation of the imager IA. This adjustment may be done automatically through a suitable imaging protocol that forwards suitable setting commands through a communication network to the control unit CC of the imaging apparatus. Alternatively, the acquisition parameters AP may be set by a user through a console (not shown) communicatively coupled to the CC. In x-ray imaging, acquisition parameters may include any one or more of the following: scan type, body part, XR source (tube) XR settings such as mA, mAs, kVp, rotation time, collimation setting, pitch, etc. "Scan type" can be helical or axial and/or may specify the region of interest (ROI) to be imaged, such as chest, lung, pulmonary embolism, cardiac, etc. "pitch" is a parameter in multi-slice spiral CT and is defined as the ratio of table increment over detector collimation. If a reconstruction operation by the reconstruction module RECON is required, such as in CT or MR or in emission imaging (PET/SPECT), this may require the specification of reconstruction parameters to accordingly adjust the reconstruction algorithm. Suitable reconstruction parameters envisaged in CT reconstruction may include any one or more of the following: reconstruction filter, reconstruction algorithm (e.g., FBP, iDose or IMR), slice thickness, slice increment, image size (in pixels or voxels, m×n) and field of view, etc.

The acquisition parameters specify how the imaging apparatus is to operate to acquire image signals which are then converted into image values. The reconstruction parameters describe how the image values are converted into other image values. Both parameters, the acquisition parameters and/or the reconstruction parameters, are thus influencing the image values or distribution thereof in the initial input imagery. The acquisition parameters AP and/or, if applicable, the reconstruction parameters RP maybe referred collectively as the "imaging parameters IP". In short, the imaging parameters IP describe how imagery was obtained.

With continued reference to FIG. 1, the application scenario for bolus tracking in x-ray based or MRI imaging is now explained in more detail. The machine learning components MLC1 and/or MLC2 to be used in embodiments separately or together in the proposed SSI are operable in two modes, in a training mode and in deployment. In training mode, which will be explained in more detail below at FIGS. 6,7 and 10, training data has been used to adjust parameters of the machine learning components, in other words, the machine learning components have been adjusted in a training phase for the intended purpose. In deployment phase, the machine learning components can then be used operating on image data not previously analyzed. In the following when explaining the bolus tracking scenario during deployment, it is assumed that machine learning components have been properly trained and are ready for use.

In an imaging scenario, a defined amount and type of contrast agent CA is administered to the patient at a suitable entry point. The femoral veins or arteries may be used in some instances.

A target location ROI is defined either manually by the user (in other words the clinician operating the imaging) or is automatically supplied by the machine learning component MLC2 that is by the context definer MLC2. For example, initial imagery earlier acquired by the patient may be used to define the target location ROI.

The user may, for instance, effect display on the display device DD of the imagery and select with a point tool such as a mouse, stylus or other the target location. Once the target location ROI, such as a part of the heart coronaries has been defined and the bolus of contrast agent has been delivered, the bolus tracking proceeds as follows.

The imager IA is operated to acquire a feed of monitoring images acquired at a suitable frequency or sampling rate. This may be one image, one frame per second (fps) but may be quicker or slower. In some exceptional instances a single monitoring image or frame may be enough if it is acquired at the right moment however, in most practical situations a plurality of images over the period of the transit time for the bolus to arrive at the target location is acquired.

At arrival of the bolus at the target location, concentration of contrast agent in the designated target region ROI will increase for some time, before it drops again. As the concentration increases, this in turn will lead to a change in intensity pattern as recorded in the acquired monitoring frames. But this pattern is in general not a fixed one as it will depend on how the CA disperses and mixes and propagates with the surrounding fluids, e.g., the blood. The shape of the bolus changes during transit time. The machine learning allows to associate various intensity patterns with the correct trigger time.

The feed of monitoring images is forwarded from the imager IA to the bolus tracker MLC2. The bolus tracker MLC2 processes the received input imagery together with optional contextual data as will be explained in more detail further below. Based on the optional context data and the observed intensity pattern in the input imagery, the decision is then made by the tracker whether or not to trigger the diagnostic imaging acquisition. The output of the tracker MLC2 is thus triggering information that can be translated by a suitable machine interface CIF of the control console CC into low level signals that then put into effect the diagnostic image acquisition. Specifically, if the analysis by the bolus tracker MLC2 of the current monitoring image reveals that not sufficient contrast agent has accumulated at the target location ROI yet, the image acquisition for the diagnostic imagery is not triggered. However, once the tracker MLC2 decides that sufficient contrast agent has accumulated as per one of the monitoring images, a trigger signal is caused by the trigger schedule output and the diagnostic imaging sequence performed by the imaging apparatus IA is triggered.

The diagnostic imagery acquired upon triggering may require for the x-ray source XR to be operated at a higher dose than those used when acquiring the monitoring imagery. In a rotational or 3D embodiment, projection imagery it from different directions q are required whilst the x-ray source XR moves along the imaging orbit OR around the target location ROI. A collimator may be used (not shown) the imagery around the target location ROI. However, this is not necessarily in all embodiments so long as the primary beam XB illuminates the target location ROI. The projection imagery 7E is forwarded to the re-constructor that uses reconstruction algorithms such as filtered backprojection to produce an axial image IM of the region of interest. This forms the diagnostic image which can then be stored in storage or can be visualized on a display device DD by suitable visualizer software. The image of the vessel VS is of interest may be examined by clinicians for steno sis, or others depending on the clinical objective.

As mentioned, the monitoring imaging acquired during the tracking phase may be lower dose compared to the dose used for the subsequent of the diagnostic image IM. In preferred embodiments it is sufficient to merely projection imagery for the monitoring imagery rather than reconstructing same into axial images which may still be done by the re-constructor which may be done in some embodiments.

Even further still, in a preferred embodiment a single projection image acquired at a time may be used. In other words, during the monitoring phase the x-ray source remains stationary and acquires at the set sample frequency single projection frames from that direction q.

In yet other embodiments, the x-ray source may be moved to different locations during the monitoring operation.

In order to reduce the amount of contrast agent administered to the patient it is proposed herein to use a spectral imaging apparatus IA. The spectral imaging data to be used as monitoring imagery may include in embodiments image data (such as CT projection image data) acquired at at least two energy levels. Other embodiments envisaged herein include, but are not limited to, CT images of the anatomy of interest ROI reconstructed from CT projection data acquired with dual-layer detector system that separate the x-ray flux at the detector into two levels of energy. In addition, spectral CT data acquired by a photon-counting detectors can be used. Yet alternative, imagers with dual X-ray tubes, each for configured to acquire imagery at different energy levels, is also envisaged herein. Spectral image raw data recorded in any of these embodiments may then be processed computationally to derive spectral imagery computationally in a spectral analysis. For instance, one approach may by to differentiate between Compton scatter and photon absorption effects or by distinguishing different material types (material decomposition). Bespoke imagery for one of the two effects or for a selected material may then be computed.

In other words, spectral imaging as used herein includes the ability of using detector hardware and/or signal processing techniques that allows to resolve the detector signals into different energy levels to so extract material specific contributions to the overall signal. Preferably, the contrast agent CA to be used has its K-edge fall within the energy range used by the X-ray source. Contrast agent imagery may then be obtained where image contrast accurately follows the current contrast agent concentration. The contrast agent imagery obtained from spectral imaging may be projection image or a reconstructed image. Preferably, such as contrast agent image in projection or imaging domain is used as the above mentioned monitoring imagery. More preferably, a few, preferably a single, projection image is acquired at a time during the monitoring and are respectively processed by the MLC2 to establish the trigger time.

It has been found that due to the spectral information encoded in the projection imagery and/or the imagery re-constructible therefrom, a lower dose of contrast agent may be sufficient to still produce clinically diagnostically valuable images and to robustly pick up the correct trigger time.

In some embodiments, but not necessarily in all embodiments and as mentioned above, the target location ROI is found automatically by the context finder MLC1. The context finder MLC1 is in general a different machine learning component than the tracker MLC2 and is configured to use contextual data such as the imaging protocol to be used for the diagnostic imaging, to automatically find the target location ROI. The target location so found may be used to automatically instruct the control console to send out suitable control signals to suitably position the x-ray source and the detector relative to the so found target location ROI. The collimator, if any, may also be adjusted accordingly to collimate around the target location ROI. Instead or in addition, the so found target location may be indicated graphically on a previous image set displayed on the display device DD during set up of the bolus tracking procedure.

The target location ROI found by the context finder MLC1 may be forwarded as input to the tracker MLC2 and this may be used as contextual information. In addition, or instead, the context finder may extract suitable bolus tracking parameters BTP which may also be supplied as contextual data, non-image input data that is, for the tracker MLC2. The bolus tracker MLC2 can thus use image information, the monitoring imagery that is, together and in combination with the contextual information to more robustly detect the suitable triggering time for the diagnostic imaging procedure. Although using the tracker and the context finder in combination as has been described, either one can be used in isolation and independently from the other. For instance, as mentioned, the tracker may use only the monitoring imagery with or without contextual data which may be provided by a user instead of the context finder. Equally, the context finder may not necessarily require for its functioning the tracker and may provide indications on the intended region of interest, the target location, for teaching purposes for instance.

The input data on which the context finder MLC1 operates may be retrieved automatically or on user demand from a suitable data base such as a medical patient record. In addition or instead, the context finder may use image data such as a scout image, pre-existing imagery or other to establish based thereon the intended target location ROI.

Figure 2:
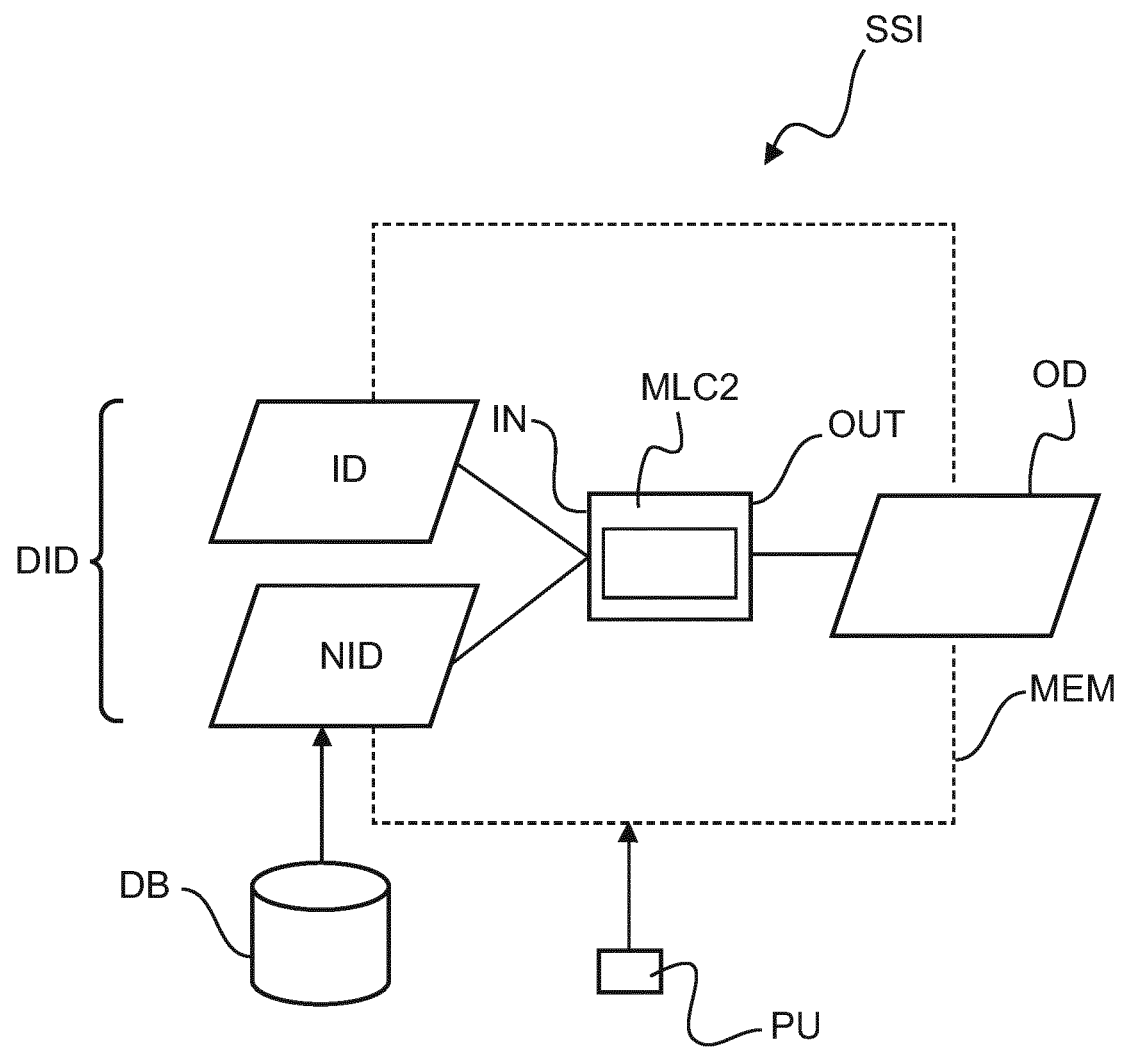
FIG. 2 shows a block diagram of a machine learning component according to one embodiment.

Reference is now made to FIG. 2 that explains in more details the aspect of the bolus tracking machine learning component MLC2. Preferably but not necessarily in all embodiments of the tracker MLC2 is arranged as an artificial neural network (referred to herein as "NN"), in particular as a convolutional neural-network (referred to herein as a "CNN"). However, other architecture such as belief networks, support vector machines (SVM) and others may also be envisaged herein, preferably, and as will be explained in more depth detailed below, where a deep architecture is used. In embodiments, the deep learning architecture includes having at least two or even more such as five, 10 or more than ten hidden layers arranged between the input layer and output layer. However, the concept deep learning applies to other machine learning components also and is not necessarily tied to NN architectures. The concept of depth in machine learning as will be used herein will be explained in more detail below at FIG. 10.

Broadly, the tracker MLC2 when arranged as a neural-network comprises a plurality of processing nodes sometimes referred to as "neurons" that can be thought to be organized in a cascaded fashion in a plurality layers arranged between an input layer IL or input interface IN and an output layer OL or output interface OUT. However, this is not necessarily spatial as the arrangement in layers of the nodes relates foremost to the manner of interconnectedness between the nodes and hence to the manner of data flow between the nodes. The architecture of the neural-network may be arranged as a suitable data structure such as, two or higher dimensional matrices arranged using for instance pointer structures or otherwise to implement the interconnections between the layers.

The machine learning component MLC2 may be held in a suitable memory MEM. Operation of the network in deployment may be beneficial implemented by a computational processing unit such as a dedicated micro-processor. Preferably but not necessarily the processor PU is arranged for parallel computing. In embodiments a multi-core design is used. In particular, graphical processing units GPU's or more recently TPU's can be used with benefit for calculations involved in neural-networks. The machine learning component MLC2 in neural-network structure is defined by a potentially very large number of network parameters that define a configuration of the network NN.

The configuration is achieved through training and will be described in more detail below. In training, the underlying mapping is estimated from the training data TD drawn from a suitable corpus(es). Assuming the machine learning component has been properly trained, deployment involves applying deployment input data DID at the input layer of the machine learning component MLC2.

The input data during deployment DID for the purposes of the tracker includes image data ID and/or non-image data NID. Image data includes imagery, existing imagery and/or in particular the monitoring imagery of the region of interest or target of location ROI. Image data is arranged as intensity values in two or higher dimensional arrays or matrices.

In x-ray imagery, each pixel value represents an intensity of recorded radiation, but the "semantics" of each pixel value may differ for other imaging modalities such as magnetic resonance MRI, or others.

The non-image data includes in particular data that describe characteristics of the patient to be imaged. The non-image data includes in particular contextual data. The image data includes in particular spectral image data as this has been found to yield good contrast results even with low contrast agent concentrations as compared to energy integrated image data.

The non-image data may also include imaging parameters IP to be used. The input data during deployment DID may also include bolus tracking parameters BTP which may itself be composed partly of non-image data or image data. In particular, the bolus tracking parameter is supplied itself by another machine learning component such as the context finder MLC1 to be described in more detail below.

The bolus tracker information in general describes the way the bolus is expected to propagate through the patient given the patient characteristics such as the fluidity or viscosity of the blood or other physical physiological peculiarities. In particular, bolus tracking information may include the expected transit time. In addition or instead, bolus tracking information may include and expected intensity pattern for the right amount of contrast agent at the target location ROI. The BPT describes behaviors of the bolus during its passage through the conduit and in particular its appearance at the ROI. In addition or instead, bolus tracking parameters BTP may include the expected transit time from entry point to the target location ROI. The BTP may allow personalization of the data. BTP may also be useful in contexts where two or more contrast agent materials are administered, e.g. in spectral or photon counting systems for material decomposition purposes. In this or similar contexts, the BTP may include two different transit times, one for each type of contrast material. Providing BTP as input to the bolus tracker as envisaged herein allows making the operation of the bolus tracker more robust. Likelihood of possibly erroneous triggering can be reduced with BTP steering the machine learning algorithm of the bolus tracker to more realistic solutions.

The input data during deployment DID is partly received from a data base either through a wired or wireless connection and is applied to the input layer of the machine learning component. In addition, the image data in particular the monitoring imagery is applied repeatedly at the sampling frequency to the input layer IN. The deployment input data as applied to the input port which may also be referred to as the global input data, propagates through the network MLC2 to produce a series of intermediate in- and output's layer and then eventually emerge as transformed global output at the output layer OL. Applying the data to the network in this manner may be referred to herein as forward propagation.

In the bolus tracking embodiment the global output data OD includes in particular a triggering schedule to control the operation of the imaging apparatus, in particular a specification to trigger the image acquisition for diagnostic imaging. However, the output data may also include other control parameters for the imaging apparatus, such as energy settings (voltage and/or amperage of the x-tube), collimator settings, and setting of any other imaging parameter for X-ray or other modalities. In embodiments, the output may be binary where for instance "0" (zero) is encoded as "holding on", that is, no triggering of the diagnostic imaging acquisition, whilst an output "1" encodes the request to trigger the diagnostic imaging operation. Other encoding schemes may also be used.

Before describing the machine learning component MLC2 in more detail in the following a few components will be described that are of particular relevance to the implementation of the machine learning component as a convolutional network or as a fully connected neural network in general. Broadly, the NN-like structure of a machine learning component may include a plurality of nodes, at least partly inter-connected and arranged in different layers. The layers are arranged in one or more sequences. Each node is an entry capable of assuming a value and/or can produce an output based on input it receives from one or more nodes of an earlier layer.

In embodiments, some or each node is associated with a certain function which can be a simple scalar value (node weight) but can also be with more complex linear or non-linear functions. A "connection" between nodes in two different layers means that the node in the later layer can receive an input from the node in the earlier layer. If there is no connection defined between two nodes, no output of one of the two nodes can be received by the other node as input. The node produces its output by applying its function to the input. This can be implemented as a multiplication of the received input by the scalar value (of weight) of the node. More than one input from different nodes may be received by a node in a later layer. The different inputs may be consolidated by a consolidating function g to produce a consolidated value and it is this consolidated value to which the receiving node applies its own function f to produce the output for the node. For instance, g may map the received inputs from earlier nodes into a sum of products (e.g., dot product) and the node's function f may then be applied to said sum of products.

A connection may have its own weight ("connection weight"). The weight is used to weigh output that travels along that connection. The consolidated function may combine all the received input for a given node using the connection weights to produce the consolidated dot product output. The connections between layers may be fixed or may vary during processing. Some layers may be fully connected whilst others may not be. Two layers are fully connected if each node in the later layer is connected with all nodes of the previous layer. In partially connected layers, not all nodes in the later layer are connected to all nodes in the earlier layer.

The outputs of all nodes of a given layer may be referred to herein as the "output of the layer" and the inputs received from an earlier layer may referred to herein as "the input of the layer".

Each layer may be represented as a matrix of two, three or higher dimensions. If the dimension is three or higher, the matrices are commonly referred to as a tensor. The nodes implemented as entries in those matrices or tensors. Each layer has a size (rows i and columns j), a depth k (which may be larger than 1) and possibly further dimensions. Alternatively, the size, depth and the one or more further dimensions may be realized by other data structures than matrices or tensors.

The MLC component in a neural-network structure includes one or more initial input layers IL and one or more final output layers OL. The initial input layers IL are where the initial image IM and the imaging parameters Ip are received, by populating the nodes or by presenting the final result for further proceeding by the conversion circuitry CC or other, respectively. Input into the input layer is the initial input and the output at the output layer is the final output. Input and output at the hidden layer may referred to as intermediate input and output.

Different types of layers may have different functions and hence apply different operations. Before explaining operation of MLC2 in yet more detail, we now turn first to discuss the different types of layers, some or all envisaged herein in different combinations and sub-combinations thereof, in particular (but not only) for networks of the CNN type or with at least one CNN subnetwork.

NN layer types envisaged herein include any one or more, or all of the following in combinations: fully connected layers FL, convolution layers CL, deconvolution layers, and pooling layers P, activation layers R.

The convolutional layer with stride >1 and/or the pooling layers may be used to implement one or more down-sampling layers. In addition or instead, down-sampling layers may be implemented through interpolation or by deconvolution.

The layer types may be grouped into units to form various operational units, for instance to implement processing at different scale levels. Although grouping layers into such units of 2, 3 or more layers can have implementational advantages when expressed as matrices/tensors and matrix/tensor multiplications, the grouping is not necessarily envisaged in all embodiments.

The pooling layer acts on a groups of inputs from a previous layer and collapses these into a single output, thus reducing dimension of the input data. The collapsing may be done in different manners, each envisaged in embodiments herein. In max or min-pooling, the maximum value or the minimum values in the respective group of inputs is produced as output, in average-pooling, an average of the values in the groups is formed to produce the output.

Turning now in more detail to the activation layer R, this may be implemented using any non-linear function, including logistic-based sigmoid functions, arctan, softmax, rectifier function ($x^+ = \max(x, 0)$), or others. An activation layer that implements the rectifier function may be called a rectified linear unit (ReLU). The activation layer R implements a nonlinear function that is applied to the values in each node to introduce a non-linearity to enable the MLC to capture nonlinear pattern. The size of the (intermediate) input layer is preserved by the rectifying layer R. Layer R also serves as an "importance filter" to remove or mitigate an input if this is below a threshold. An input from a node may be completely annulled and hence not forwarded at all to the next layer despite there being a connection. The node is then said not to "fire" and this event is then recorded by forwarding "zero" to the next layer. The proportion of not firing nodes in a given configuration may be expressed as the sparsity of the MLC.

Turning next to fully connected layers FC, the layers envisaged herein in MLC are not necessarily fully connected although in embodiments the network MLC does include two or more fully connected layers. Fully connected layers are shown as FC in FIG. 3 above. The fully connected layers FC represent more traditional, non-convolution NN components where each node is associated with its activation function and a weight. Each node in one layer of the FC receives an input from all nodes in the previous layer each weighted according to the respective weight for the connection, as explained above in the general introduction. This total input is then summed and evaluated by an activation function layer R. The activation function layer is applied to the weight of the respective node to produce a node output which is passed onto nodes in the subsequent layer. The advantage of using FCs are to model more complex, non-linear patterns.

The convolutional layer CL and de-convolutional layers are examples of non-fully connected layers. More particularly, these layers are not fully connected to all nodes of the earlier layer. In addition, the connections vary when processing the (intermediate) input from the earlier layer.

In convolution layer CL, each node of the intermediate output is obtained by convolving the convolution layer with a sub-group of nodes of the earlier layer, thus involving only a sub-set of all possible connections. The connections are then redefined to single out a new group of nodes for the next intermediate output layer and so on, until the whole (intermediate) input layer has been processed.

The convolutional layers CL may be structured as matrices with size preferably odd-numbered, such as 3×3 or 5×5 with a center position. The convolutional/de-convolutional layer may also have a depth that corresponds to that of the depth of the intermediate input to which it should be applied.

The size of the convolutional/de-convolutional layer is in general smaller than the size of the intermediate input on which it acts. Just like in conventional convolution, the convolutional layer may be conceptually thought to slide over its (intermediate) input layer and is applied selectively to different groups of nodes to produce filtered nodes as an (intermediate) outputs. The convolving operation itself may involve forming sums of products between the nodes of the convolution layer and/or all nodes within the instant group in its intermediate input layer. The filtered node is the central node of the odd-sized matrix of the convolutional layer.

The shifting to a new group of nodes in the processing of the convolutional layer may be conceptually understood as a sliding the convolution layer CL with stride=n (n being a natural number) over the (intermediate) input to produce the (intermediate) output for each group nodes, respectively. The stride is a design parameter of the CNN that indicates the extent of each shift. For instance, stride n=1 means that the new group is obtained by effectively shifting the layer CL by one node when redefining the connections for the next group of node whose values are to be convolved to obtain the value of the next (intermediate) output node. For stride n=2, one column or row of nodes is skipped and accordingly for n>2. It will be understood that, instead of the sliding window approach described above, the input layer to be processed by the convolution layer may be instead broken up open into parts (tiles), and each of these are then convolved with the convolution layer separately.

Zero padding may be used if the convolutional layer extends beyond the outermost nodes of its intermediate input layer on which it acts. The convolutional/de-convolutional layer may be applied in sequence as described or may be applied in parallel in the whole of the intermediate input layer.

The de-convolutional layer is essentially an inverse operation to the convolution caused by the convolution layer CL. Whilst the convolution layer maps, initially, from pixels to features of progressively higher level, the deconvolution operation maps features back down to pixels. Functionally, the deconvolution can be formulated in terms of convolution operations as used in the convolution layer discussed above which are then summed, optionally with respective local zero paddings around processed locations. See for instance section 2 in M D Zeiler et al in "*Adaptive Deconvolutional Networks for Mid and High Level Feature Learning*", 2011 International Conference on Computer Vision, Barcelona, Spain. The de-convolutional layer D may also be represented as a matrix with appropriate depth.

As such, the convolutional and de-convolutional layers do in general preserve the size of their (intermediate) input, if stride is 1. Otherwise, they can act as downsampler layers. The down sampling is similarly structured as the convolutional/de-convolutional layers but they act on its input data differently. The down-sampling/up-sampling layer (also referred to herein as simply "down"- or "up-samplers") may be odd- or even-sized. The down sampling layer lumps together a group of nodes in the earlier layer to produce a single node for the subsequent output layer, thus reducing the spatial (less rows and/or columns) of the (intermediate) input layer. This can be done by forming an average or by picking the maximum/minimum value or any other designated value from the group of nodes covered. The size of the group corresponds to the size of the down sampling layer.

The up-sampler acts quasi-inversely to the down-sampler and produces at its output a larger set of nodes, preferably by interpolation between input nodes. Convolution/Deconvolution and the up-sampling/down-sampling functionality may be combined in the same layer. For instance, convolution and down-sampling may be achieved as a convolution with stride >1, such as 2 or larger. In a similar fashion, the deconvolution may be combined with the up-sampling functionality.

Figure 3:
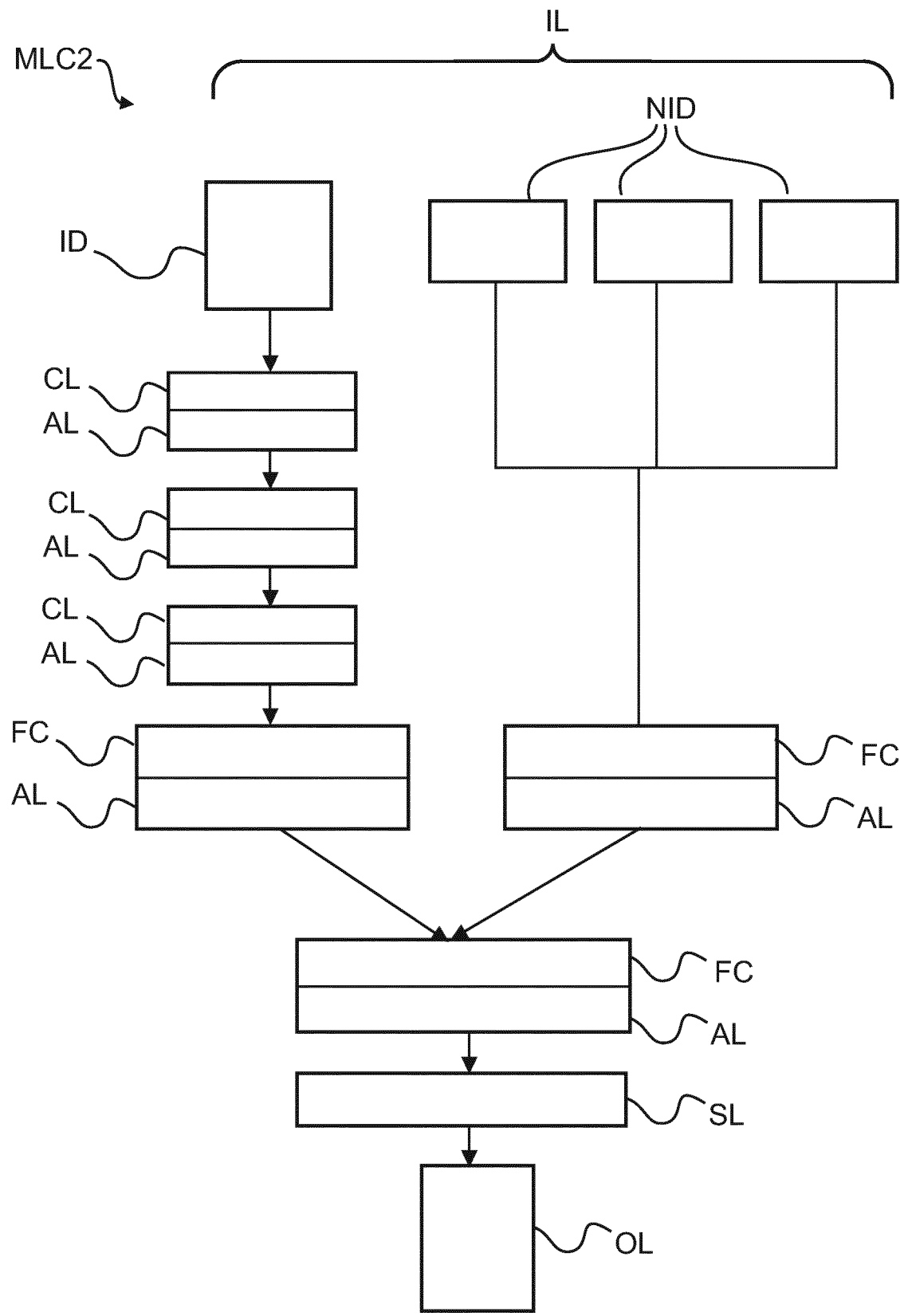
FIG. 3 shows a block diagram of an artificial neural-network embodiment of a machine learning component according to one embodiment.

Referring now to FIG. 3, this shows a feed-forward neural-network architecture as envisaged herein in embodiments for the tracker MLC2. The network is of the hybrid type and includes a convolutional CNN sub-net portion and a fully connected portion sub-net and a combiner stage to combine the outputs from two sub-nets. The global input data during deployment DID supplied to the input layer IN may include the monitoring image data ID and optionally contextual non-image data NID as mentioned above.

The image data ID includes in particular the feed of monitoring images (frames) although in exceptional circumstances a single monitoring image may suffice to establish the trigger time. The monitoring image(s) are preferably spectral images in the projection or image domain. Alternatively, conventional energy integrated imagery may be used. Preferably, projection domain imagery is used, and more preferably still, a single projection image is acquired at a time during the monitoring.

The non-image data NID may include any one of patient clinical data, imaging parameters IP, or at least a part of the BTP. The BTP may comprise an image data component to describe the expected intensity profile of the bolus at the location of interest. In this case, the image part of the BTP is then processed herein as part of the image data ID. The BTP or parts thereof may be supplied by the context finder MLC1. The non-image data forms contextual data, and may also include vital sign measurements, such as heart rate, blood pressure, etc. In addition or instead, the BTP may include expected time of arrival, possibly in dependence on the specific contrast agent used, and/or in dependence on patient data, such as the vital sign measurement. The image and non-image data may be applied to a single input layer however preferably separate, dedicated input layers are used for each. Preferably there are also separate sets of hidden layers for the non-image data and image data, respectively. In embodiments therefore the MLC2 may be thought of as two separate convolutional neural-network architectures combined. In fact, the non-image data may be processed by one sub-network (which is either fully connected or a CNN) and the image data may be processed by another sub-network that is preferably a CNN. The respective outputs may then be merged into third component that acts as a combiner stage. The combiner stage that may include a neural-network architecture on its own, not necessarily a CNN one. Specifically, the sub-network that processes the image data is preferably a CNN whilst the sub-network that processes the non-image data may be a fully connected, NN, so is not a CNN.

Turning now in more detail to the embodiment in FIG. 3, in embodiments the sub-network for the processing of the non-image input data may be implemented as a single fully connected layer FL whose output is passed through an activation layer as shown on FIG. 3. Alternatively, two (or more) fully connected layers are arranged in series, some or each having their respective output processed by a respective activation layer AL.

The processing of the image data on the other hand may be implemented as a CNN that includes one, two or three convolutional layers CL some or each having its own activation layer AL. The intermediate output emerges at the activation layer of the final convolutional layer FL.

The intermediate outputs of the two sub-networks for the image data and non-image data may then be together fed into one or more fully connected layers at the combiner stage. This output at the output layer may then be translated into control commands and forwarded to the control console and the imaging interface CIF to the imager to trigger the imaging for diagnostic purposes. If a binary output is required to encode whether or not to start the diagnostic imaging, a downstream sigmoid layer SL may be used that converts the output as "0" or "1". By convention, zero may indicate not to start the diagnostic imaging, whilst unity encodes the stating signal for the diagnostic imaging. Other encoding may be used instead. The use of the sigmoid layer essentially effects a thresholding which is of benefit one the earlier layer produced outputs in terms of probabilities to start diagnostic imaging or not. The sigmoid layer may then be used to trigger imaging only if the probability is higher than a threshold p % that the current monitoring image represents a sufficiently high amount of contrast agent at the location of interest. The threshold may be set to, for example, p=95% or other suitable value. The percentage threshold p may be user adjustable. In alternative embodiments, there is no thresholding. Instead, the probabilities are the final output of the tracker MLC2 and are displayed to the user on the display device DD. It is then the user who manually triggers the diagnostic imaging if the probability is thought sufficiently high.

The architecture as shown in FIG. 3 is an exemplary embodiment and other combinations of CNN and fully connected NNs are also envisaged herein in embodiments. Also, the exact order and number of layers as described may vary and all such permutations and variants are envisaged herein for architectures in different depths with depth at least 2, 5, 10 or more.

Figure 4:
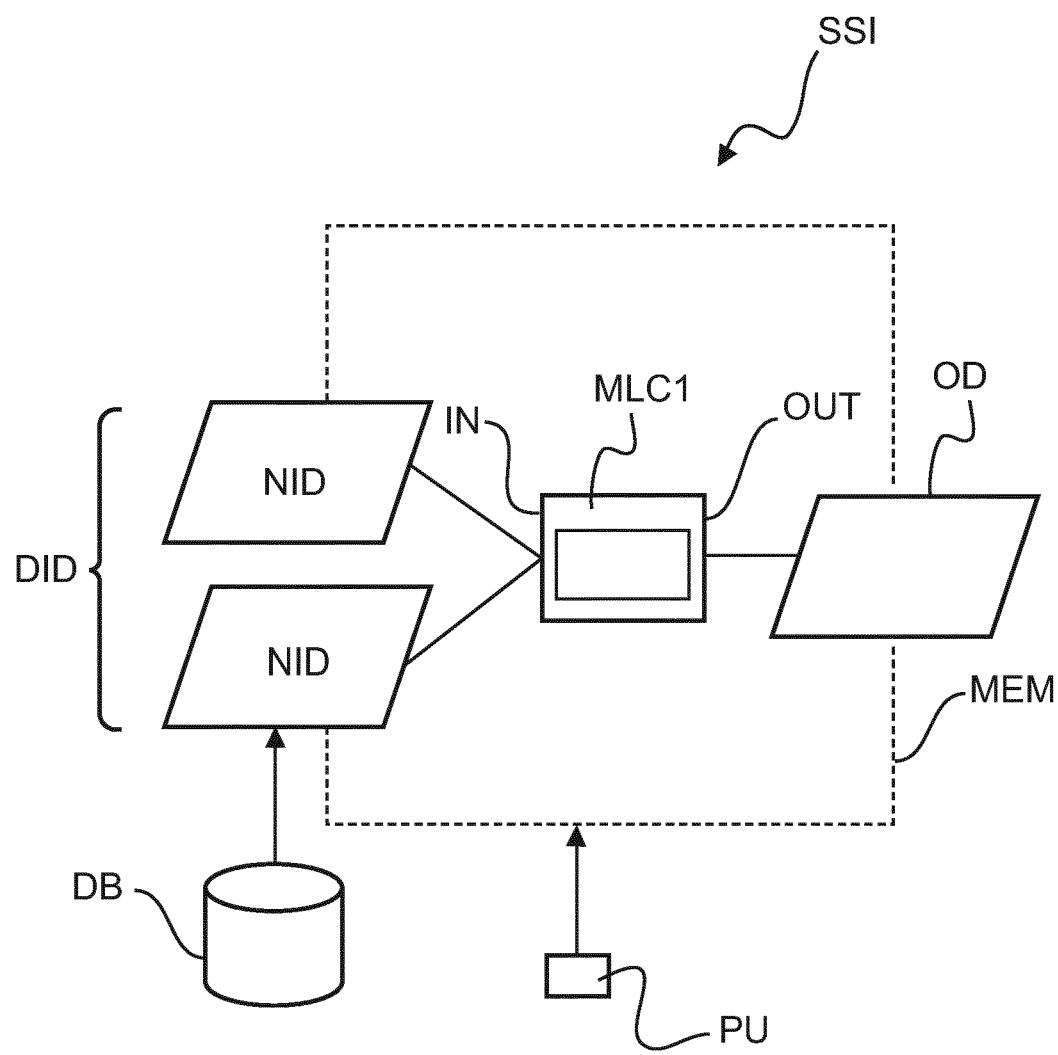
FIG. 4 shows a block diagram of a machine learning component according to a second embodiment.

Reference is now made to the block diagram in FIG. 4 that provides more details on the machine learning component MLC1 according to the context finder embodiment. The basic components are as described above in FIG. 3, with like numerals indicating like components and data.

The context finder may also be implemented as a neural-network architecture including convolutional network CNN. As mentioned above in relation to FIG. 2, other machine learning technologies than neural-networks may also be used instead.

The input data during deployment DID again comprises image data ID and/or non-image data NID. As discussed above in relation to the bolus tracker, the non-image data forms contextual data. The contextual data may further include vital sign measurements, such as heart rate, blood pressure, etc.

The image data may for example include a first image such as the first CT scan of the anatomy of interest. This first image has a field of view wide enough to cover a body area to include the ROI. The non-image data may include the scan protocol that indicates which region of interest is to be imaged.

The input data may further describe the patient such as in medical records or other clinical data or in general contextual data.

During deployment the input data DID supplied to the input layer of the network MLC1 and is propagated there through to obtain an output layer OUT. The output data in this embodiment includes an indication of the target location ROI for instance in terms of co-ordinates in the image data ID supplied at the input layer. In other words, the location of the ROI is automatically delivered by the context finder MLC1, preferably in terms of coordinates for the specific patient to be imaged. This automatic ROI-finding capability may be used with benefit in multi-ROI imaging scenarios, where the proposed system is cable to adapt the ROI location to patient parameters. In addition or instead, the output data may specify the BTP that describes expected properties and behaviors of the bolus at the target location ROI.

Figure 5:
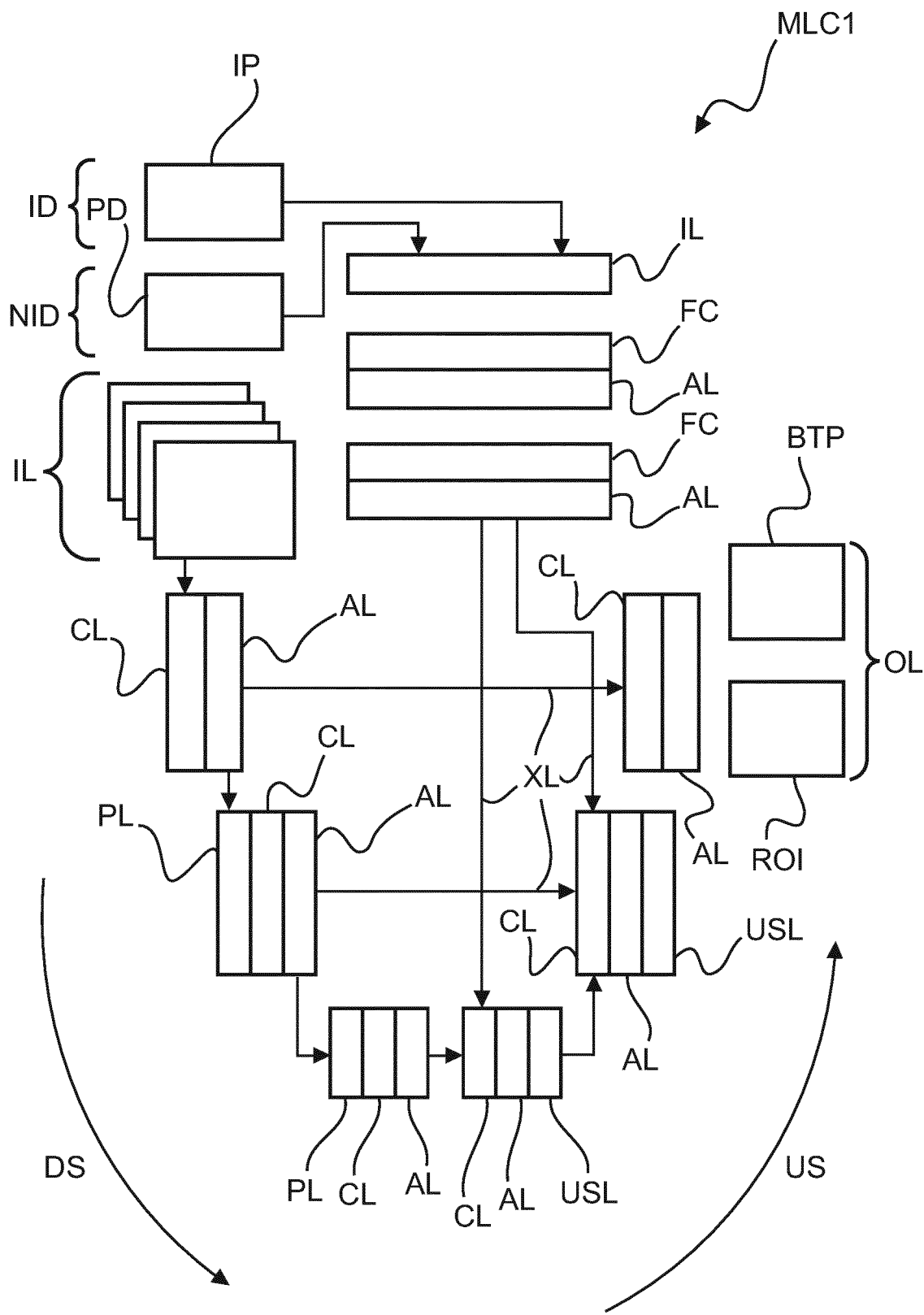
FIG. 5 shows a block diagram of an artificial neural-network embodiment of a machine learning component according to one embodiment.

Referring now to FIG. 5 this shows a particular embodiment using a neural-network architecture for the context finder MCL1.

As before in FIG. 3, the overall network structure may be comprised of sub neural-network structures, one for the image data ID and one for the non-image data of the global input data during deployment DID.

The non-image data NID such as the intended imaging protocol IP and/or patient data PD, medical records etc., in general, data that describe the patient to be imaged, may be fed into a feed-forward fully connected network comprising one or two fully connected layers FL. In the embodiment in FIG. 5, two fully connected layers FL in sequence are shown, each having an activation layer AL. This sub-network processes the non-image data. The output of this sub-network may then be fed into a second sub-network that is configured to process the image data.

Turning now in more detail to the second sub-network, this may be arranged as a convolutional network architecture. Specifically, in embodiments, and as shown in FIG. 5, a "U-net" architecture is used. U-net networks have been described for instance by O. Ronneberger et al in *"U-Net: Convolutional Networks for Biomedical Image Segmentation"*, published in Navab N. et al (Eds) *"Medical Image Computing and Computer-Assisted Intervention—MICCAI 2015, MICCAI 2015. Lecture Notes in Computer Science"*, Springer, Vol 9351, pp 234-241.

More generally, and not necessarily in U-net architecture, the network that is configured to process the image data ID may comprise two processing strands, one down-sampling strand DS and one up sampling strand US, the stands arranged in sequence, the US downstream of the DS. A reversed arrangement may also be envisaged in alternative embodiments.

Broadly, in the down sampling strand DS, the data dimension of the input image data is gradually reduced by one or more down-sampling layers. This allows achieving a low dimensional representation of the image data to better combat undesirable over fitting effects. In the subsequent up sampling strand, up-sampling layers are used to up-sample the data dimension to rematch, in embodiments, with the dimension of the global input image data as received at the input layer IL.

The down sampling strand DS may include one or more down sampling layers arranged in sequence some or each having its activation layer. The down sampling layers may be implemented as convolutional layers with stride larger than one and/or by using one or more pooling layers PL. The pooling layer, if any, may be combined with an associated convolutional layer CL which may or may not have stride larger than one.

At the last layer of the down sampling strand DS, the emerging intermediate output is then fed into the up sampling strand US. As mentioned, the up sampling strand is constructed from a sequence of (one or more) up-sampling layers. The number of up sampling layers in general matches the number of down sampling layers in the down sampling strand DS in order to achieve the same dimension at the global output. However, this may not be necessarily so in all embodiments where the dimension of the output at the up-sampling strand differs from the dimension as received at the input layer.

The up sampling layer USL may be arranged as de-convolutional layers, or as interpolating layers, some or each having attached an activation layer AL. In embodiments (further) respective convolutional layers CL are combined with the up sampling layers USL, optionally with an activation layer interposed as shown in FIG. 5.

In embodiments, the intermediate output at the conclusion of the up-sampling strand US is then combined with the output of the non-image data processing network component in combiner stage to be processed together. The combiner stage may be formed by a separate layer such as the convolutional layer with its activation layer. The combiner stage connects to the output layer OL where the final output emerges in terms of any one or both of the BTP and the indication of the region of interest or location of interest that is to be imaged.

Optionally, one or both of the final outputs, the BTP and/or the ROI, may then be fed as initial input into the tracker network MLC2 as previously described in FIGS. 2 and 3.

In addition or instead of combining the non-image and image data outputs at the combiner stage as described above, the network MLC1 may include one or more cross-feed links XL that feed from the intermediate output of the non-image processing sub-network into the up-sampling strand (as shown in FIG. 5) and/or into the down-sampling strand. More specifically and in embodiments, the non-image data is fed in plural such crosslinks into some or each layer of the up-sampling strand US or down-sampling strand DS.

In addition or instead of such crosslinks, there may be one or more image data cross feed links that feed from some or each layer (in particular from the activation layers AL) in the down-sampling strand into respective layers of the up-sampling strand US, in particular into the convolutional layer(s) CL therein. The cross-linking of the two strands allows configuring the network MLC1 for multi-scale recognition.

The architecture as shown in FIG. 5 is an exemplary embodiment. Other combinations of CNN and fully connected NNs are also envisaged herein in alternative embodiments. Also, the exact order and number of layers as described may vary and all such permutations and variants are envisaged herein for architectures in different depths with depth at least 2, specifically up to and including 5 or, yet more specifically, up to and including 10 or more.

As a variant, the architecture of FIG. 5 may be used instead or in addition in the bolus tracker MLC2. Equally, the architecture of the bolus tracker as per FIG. 3 may be used instead or in addition for the context finder MLC1.

Figure 6:
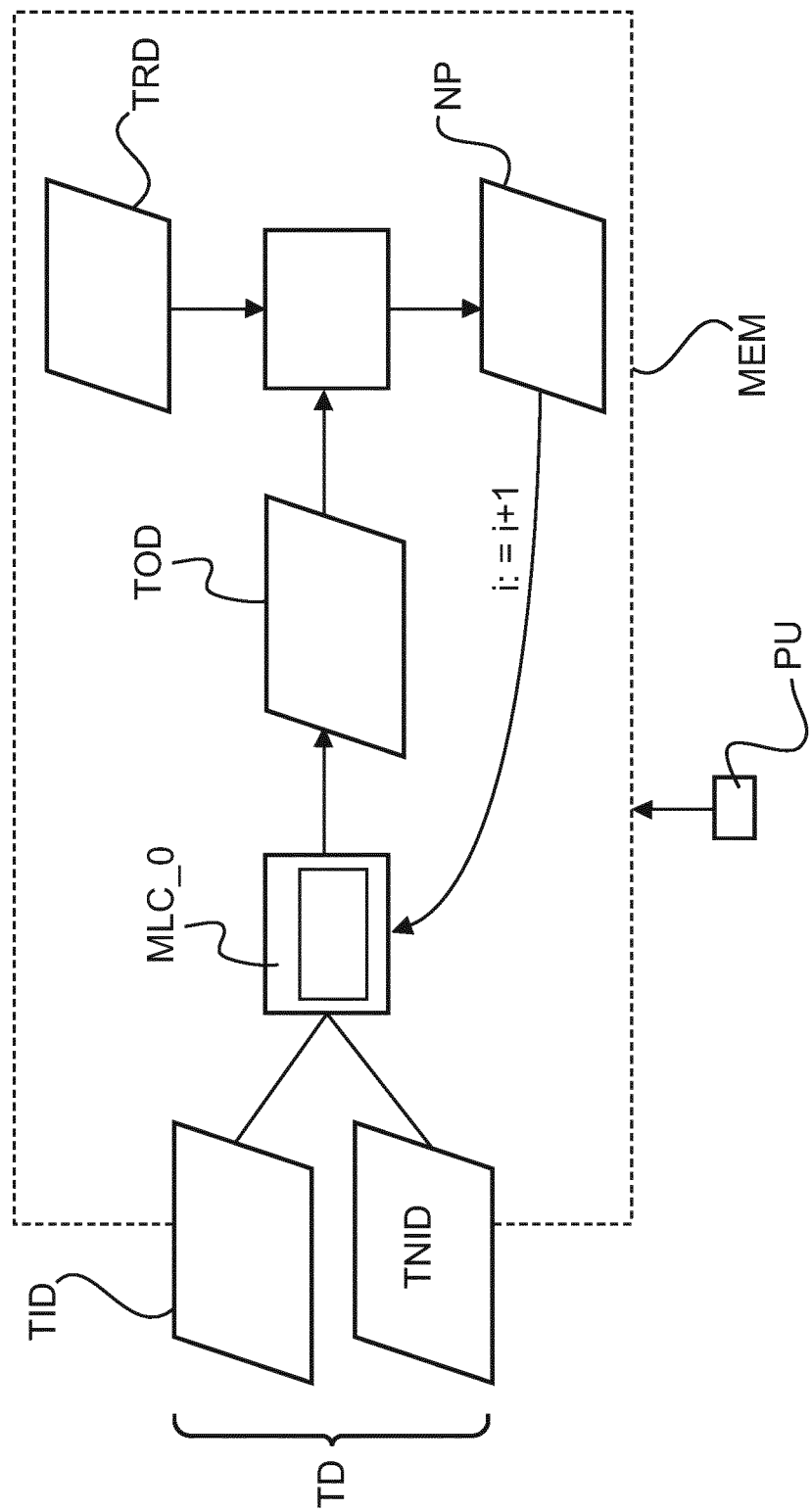
FIG. 6 shows a system for a machine learning component according to one embodiment.

Referring now to FIG. 6 this shows a block diagram of a systems for a training machine learning component MLC1 as described above in FIGS. 4, 5.

The training data TD received at the input layer includes training image data TID and/or non-image data, the later including in particular the imaging protocol that indicates which ROI is to be imaged.

Before training starts, the machine learning component is set up in a chosen model, e.g., a fully connected NN, a CNN architecture or other, and this architecture is then initialized with initial model parameters, for example random parameters or with identical parameters. In other words, and using the CNN as an example, weights for the node connections, filters, etc. are pre-populated. The chosen architecture in CNN defines for example the number of hidden layers, the type of activation functions, the size of and shape of the convolution layer filters (if any), etc.

The learning algorithm is then run on a suitable processing unit PU. The learning algorithm may be formulated as an optimization problem. The goal is to optimize an objective function. Each sample in the training data is applied to the machine learning component as initialized. The machine learning component produce at its output layer training output data TOD which is then compared with reference training data TRD by means of the objective function. Most likely, an error may be incurred between the reference data TRD and the target training output data TOD and this error is measured by the objective function. The optimization algorithm then re-adjusts the current (initial) parameters and re-populates, if required, the network with new or updated model parameters NP. The procedure is then iteratively repeated and new items of training data TD are fed into the machine learning component. During the course of the iterations, the network parameters are readjusted to eventually arrive at a fully trained version for the context finder MLC1. The training reference data TRD may include in particular historic BTP and suitable identifications of the ROI, in terms of image coordinates or otherwise, as were used in historic sessions bolus tracking sessions.

Figure 7:
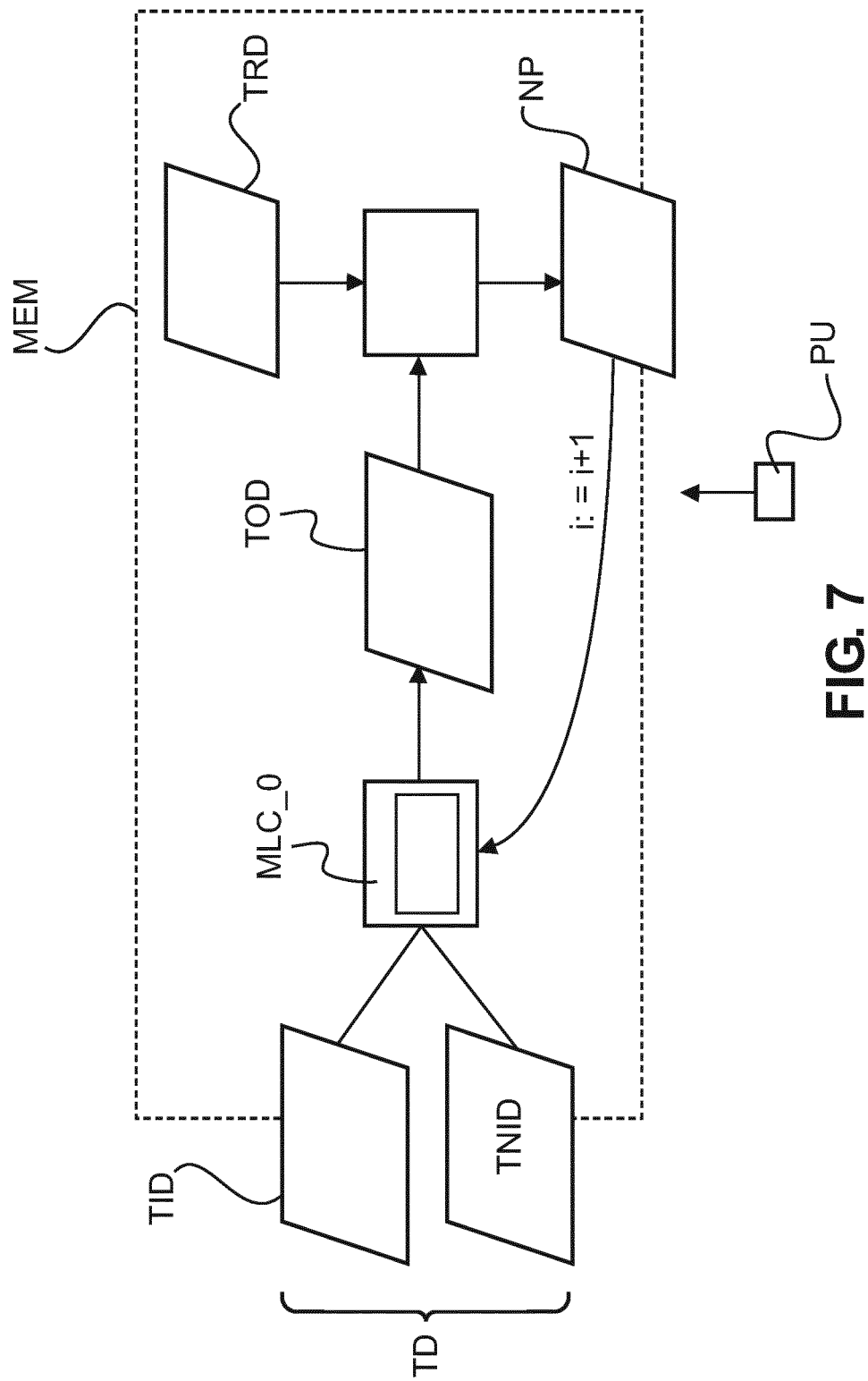
FIG. 7 shows a system for training a machine learning component according to one embodiment.

A similar training procedure is outlined in FIG. 7 for the tracker embodiment MLC2. The training data TD in this case includes monitoring imagery acquired in historic (earlier) bolus tracking sessions for other patients. In particular, the monitoring image that caused the diagnostic image acquisition in those historic sessions is used as training image data. The training input data may include contextual data NID such as the BTP and, optionally, clinical data of the patient as described above. The reference training data RTD includes, in particular, the trigger times in those historic sessions. Training proceeds as described above in relation to FIG. 6. Although the tracker is preferably envisaged to operate on projection images only in deployment, in training it may be beneficial to provide as training input data, both, projection imagery and the associated reconstructed image in image domain.

It will be understood that the training systems described in FIGS. 6 and 7 may be implemented using GPU's or similar processors, preferably configured for parallel computing such as multi-core processors and others, much has been described above in relation to deployment.

The learning algorithms used to adjust the parameters of the machine learning component MLC1 and MLC2 will depend on the architecture chosen. For instance, for neural-networks including convolutional networks as mainly envisaged herein gradient and descent optimizing schemes such as the backpropagation algorithm may be used. For other architectures, such as decision trees or support vector machines, different optimization schemes may be called for.

The overall respective input port/interface IN in the support system SSI and the training system allows applying the input data (for training or deployment purposes) to the input layer IL. Similarly, the overall output port OUT reads off the output data from the respective output layers OL. The ports IN, OUT may be logically or physically combined with the respective layers IL, OL.

The learning phase and the selection of training data will now be described in further detail at FIG. 10 below.

Figure 8:
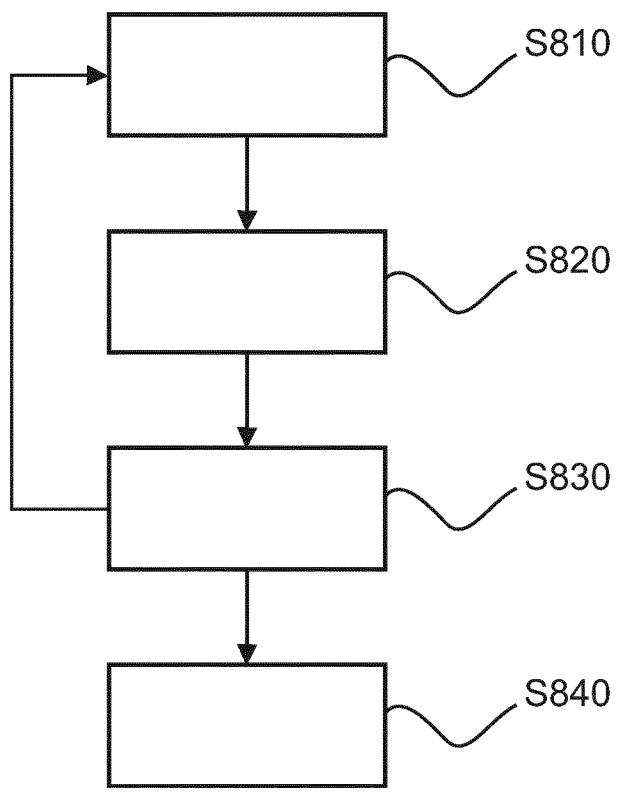
FIG. 8 shows a flow chart of a method of supporting imaging according to one embodiment.
Figure 9:
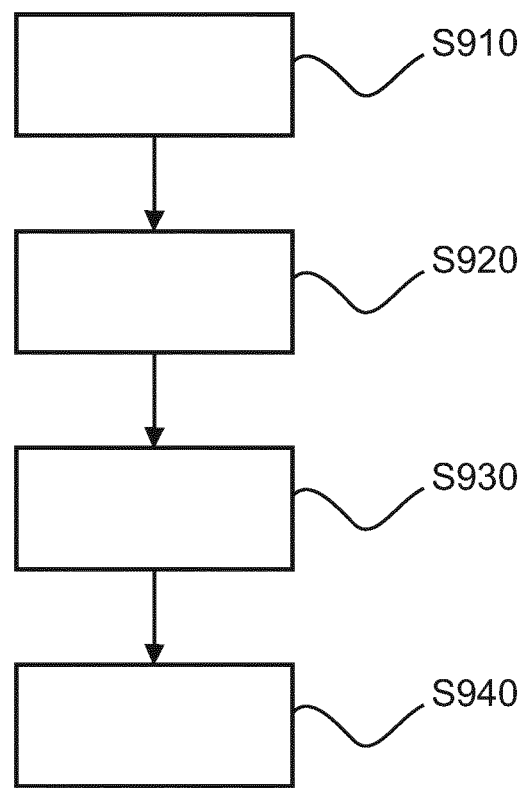
FIG. 9 shows a flow chart of a method of supporting imaging according to a second embodiment.

Turning now first to FIGS. 8 and 9, these show flow charts describing methods of operation underlining the above described pre-trained machine learning components MLC1, MLC2 in FIGS. 2-5. However, it may be understood that the following methods as presented in FIGS. 8 and 9 may also be understood as teachings in their own right and may in particular be not necessarily tied to the architectures existence described above in FIGS. 2-5.

Turning now first to FIG. 8, this describes a method for supporting imaging, in particular, in the bolus tracking embodiment or similar applications where the propagation of a substance through a conduit towards a location of interest is observed.

At step S810 input data is received. The input data includes, in particular, an input image that is acquired by an imaging apparatus such as an x-ray apparatus of the target location. Preferably the X-ray imaging apparatus is configured for spectral imaging. Although a single image may be sufficient in some instances usually feeds of a plurality of images acquired in a time series is received at a pre-set or adjustable sampling frequency.

The monitoring images may be image domain imagery re-constructed from projection imagery: Preferably however, projection images themselves may be used. In one embodiment, a single projection image at a time is acquired at the required sampling frequency. The projection images may be acquired from fixed direction throughout the monitoring phase although change of direction may still be envisaged in alternative embodiments.

In other embodiments a change from one imaging direction to another by movement of the x-ray source for instance is also envisaged.

At step S820, the monitoring imagery is then processed by a pre-trained machine learning component.

At step S830, the machine learning component MLC2 produces an output that indicates an arrival of the propagating substance at the target location.

The output may be binary and may specify whether or not an imaging operation of the image apparatus is to be carried out. In particular, the triggering of a diagnostic image operation is envisaged.

In a subsequent step S840, the diagnostic imaging may then be started if the output data so indicates. If the output data indicates that, based on the current monitoring image, no diagnostic imaging should be started, the process flow of the method returns to the receiving step S810 and the processing repeats for the a newly received monitoring frame in the feed.

In diagnostic imaging, as opposed to the monitoring phase, imagery is acquired usually at a higher dose than used for the sequence of monitoring images. In CT for instance, the triggering event causes the x-ray source to move, in a not necessary complete revolution, around the location of interest to acquire plurality of projection images from different directions at the required dosage which is then assembled into an axial image by the re-constructor. The imager IA used for acquiring the monitoring images is preferably suitably equipped and configured for spectral imaging and the monitoring images received at step S810 are spectral images, preferably adapted to the material characteristics of the contrast agent used.

It may be understood however that the triggering command is sent to a second imaging apparatus to perform the diagnostic imaging whilst the monitoring imagery is acquired by another imaging apparatus. Preferably, however, the same imaging apparatus is used for both the acquisition of the monitoring imagery and the diagnostic imaging.

The output data produced by the machine learning component at step S820 may need to be translated into lower level hardware commands and can be done by suitable interfaces to actually effect the commencement of the diagnostic imaging operation, in particular the diagnostic imaging acquisition operation.

It will be understood however that the output data produced by the machine learning component may also be envisaged for other control operations of the imaging apparatus other than merely triggering an image acquisition sequence such as stopping an ongoing image acquisition, changing imaging parameters during an ongoing acquisition (e.g., from high energy to low energy), or other.

Turning now to FIG. 9 this relates to a method of operation to support imaging in particular the context of the described context finder or similar applications.

At step S910 input data is received. The input data may include in particular a specification of an imaging operation that is to be carried out. In addition or instead, the input data describes the object, that is the patient to be imaged in terms of general physical characteristics and/or vital signs such as blood pressure, heart rate etc.

In step S920, the input data is then processed by a pre-trained machine component to obtain output data, substantially as described above at step S820.

In this embodiment the output data that is indicative in embodiments of the target location within the patient that is to be imaged. It may indicate for instance, in terms of image co-ordinate, neighborhood or a center of anatomy of interest such as the coronaries, liver etc. In addition or instead, the output data may comprise the above mentioned BPI that is the bolus tracking parameters.

The bolus tracking parameters PTB are parameters that are capable of establishing whether the bolus has arrived at the target location. In particular, BTP describes at least partly a manner of propagation of the bolus towards the target location. These manners of propagation include for instance, the expected arrival time, for instance, in terms of seconds or minutes. In addition or instead, the PTB may also describe an expected intensity pattern at the target location in terms of intensity profile curves. The expected intensity pattern corresponds to the amount, in absolute terms or in concentration, and/or on the shape of the bolus or parts thereof when arriving at the target location.

The output data so obtained may be output at step S930 for further processing, storage or otherwise.

One application of the output data produced at step S930 may include forwarding this input data at step S940 for use in the above described bolus tracking method in FIG. 8. In this embodiment the output data produced is received as contextual and/or image data at receiving step S810 as described above.

Figure 10:
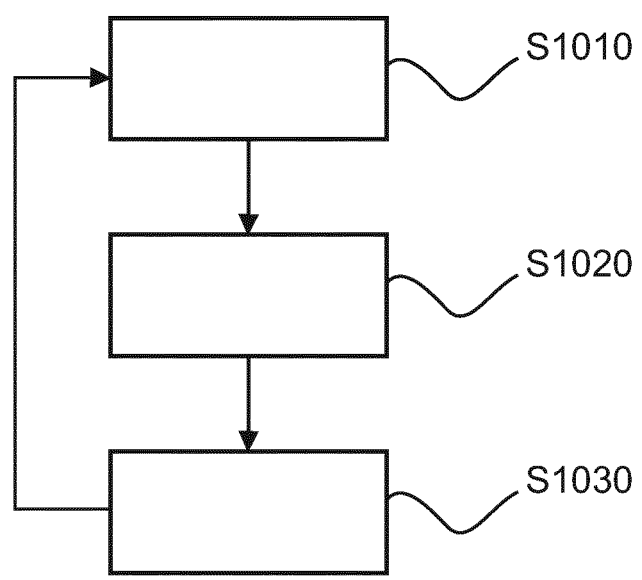
FIG. 10 shows a flow chart of a system of training a machine learning component.

Referring now to FIG. 10, this describes in more detail processing steps underlying training of the machine learning components as discussed above. In particular, the following steps also provide more details on the training systems described above at FIGS. 6,7. In the training or learning phase, a machine learning component is a model that is to learn a tacks, such as bolus arrival detection for MLC2 or ROI location finding for the context finder MLC1. In more detail:

At step S1010, the training data TD is provided to train the machine learning components described above, with the components suitably initialized.

Broadly, the training data comprises the training input data that is fed into the machine learning component and target data v' associated with the training input data v. The target represents the correct response given the training input data. The training data thus comprises batches of data pairs (v, v') that are fed either in sequence or in parallel into the machine learning component to be trained.

In the bolus tracker MLC2 training or in similar embodiments, the training input data comprises as discussed above previously monitoring image data which were used as a decision basis to trigger diagnostic imaging and contextual data such as patient clinical data, patient characteristics (age, sex, weight, etc.), or vital signs previously measured and in embodiments earlier relied on bolus tracker parameters or imaging parameters.

The target portion of the data in this embodiment includes then the suitably trigger times, that is for instance the time of arrival of the respective boluses in those earlier cases and, in particular, the monitoring image that caused in the historical cases the respective diagnostic imaging triggering.

Interestingly, in embodiments it is not necessary for the training imagery that was used as decision basis to have the respective region of interest designated or otherwise marked up. For it is the image globally that is being used to learn the correct triggering or imaging control parameters. However, the training imagery for this embodiment may still include such marked up designations such as outlines or other graphical visualization of the respective location of interest.

The training data for training the context finder MLC1 embodiment includes the earlier scan protocols used and/or patient clinical records, other clinical data etc., and, optionally, earlier imagery relied on in those historical cases. Targets in this embodiment are then the relied on BTP and/or specification of the respective regions of interest. The region/location of interest can be characterized graphically and/or by image co-ordinates. For instance, neighborhoods may be defined around the region of interest such as circles, ellipses or squares or otherwise and/or a co-ordinate for a center portion of the respective region of interest may be used instead or in addition.

It will be appreciated that the procuring of the training data can be readily obtained without much manual effort or no manual effort at all from existing, preferably digital records, of successful angiographic imaging session as have been conducted in clinics around the world over the previous decades. In this manner, potentially tens or hundreds of thousands of pairs of such training data can be obtained. Much of the training data information discussed above is for instance encoded already in header files of the image data itself as is the case for images stored in the widely used DICOM standard. In this case and similar cases, a data grabber, such as a scripting program, may be used to automatically extract the training data from the header files or from associated health records of patients. Data grabbers may access HISs or other data repositories such as a PACS. Suitable scripting languages such as Pearl, Python, PHP or others may be used to formulate such data grabbers.

For example, header files or other records relating to historical angiographic imaging sessions, will indicate when the procedures had started in those historical sessions and when the diagnostic imaging was then triggered, which furnishes, by a simple subtraction, the target data for the trigger time.

Once the training data is obtained and identified, it may be transformed into a structured format such as numerical form. The training input data v, v' may be formatted preferably in vectors of two or higher dimensional matrices. The matrix format is of particular advantage when convolutional network architectures are to be trained as operations during training (and in fact deployment) of CNNs may be formulated in terms of vector and matrix or tensor operations.

In particular, in order to process in training (but also in deployment), image data and non-image data together, as was done at the merger or combiner stages of the networks in FIGS. 3,5, the non-image data may be reformatted into pseudo-images that can be processed together with the image data. Forming of such pseudo-imagery may be done by encoding the data numerically and then populating these numbers into 2 or higher dimensional matrices ("data volume"). In particular, respective layers of such a data volume may be populated with identical copies of respective non-image data items, and respective copies of the next data item are populated into the next layer and so on. The layers through the volume then each hold copies of the respective data items with different data items arranged along a depth dimension through the non-image data volume. In this or similar manners, the non-image data may then be processed together in neural network architecture, in particular CNNs. Other reformatting techniques are also envisaged.

In step S1020, training data is then fed in sequence or in parallel into the respective learning components to obtain training output data.

In step S1030, an optimization algorithm is then performed to effect the learning. In the optimization algorithm, model parameter(s) of an initial model of the machine learning component are adjusted to arrive (possibly after one or more iterations) at the final, fully trained machine leaning component MLC1, MLC2, ready for deployment. Learning may be a one-off operation or the fully trained machine leaning component MLC1, MLC2 may be further trained in one or more additional training phases once new training data becomes available. The ML components MLC1, MLC, once trained with sufficient amount of training data, may then be applied in deployment to new input data, that is, data that is not part of the training data.

Below further details are now provided on the above mentioned steps of method in FIG. 10.

Initially, a machine learning prototype, a learning model is set up. The learning model, such as the above discussed CNN, NN, SVM or other, is initialized with parameters as part of the setup. The model may be populated with random values or with constant values in the initial setup. These initial parameters are then to be adjusted during the training. The training procedure itself may proceed iteratively in a set number of steps or until a stopping condition is fulfilled.

Some training algorithms envisaged herein can be formulated as optimization problems where the optimization function is optimized. Optimization includes minimization or maximization of the objective function. The objective function is a function of the network parameter and maps preferably into a number. Optimization includes finding the minimum or the maximum of the objective function by adjusting the parameters of the machine learning component according to the optimization algorithm used. It is not necessarily the global optimum that is found in this way. Finding a local optimum (that is, a local minimum or local maximum) may be sufficient in most cases. Also, iterations of the algorithm to a local or global optimum may not be run until full convergence but convergence is measured against a threshold, and iteration is stopped once the threshold is respected. Alternatively, iterations but be may be aborted earlier still after a number of iteration cycles, as required.

In some optimization problems in relation to the training of machine learning components, these can be formulated in terms of a loss function $f^L$ that is to be minimized and this will be used in the following with the understanding that the dual formulation in terms of a utility function to be maximized is also envisaged herein.

In general, the loss function $f$ is a functional that maps v,v' to a number. The loss function $f^L$ is configured to quantify the error 4 between the target v' and the training output data, which may be formally written as "M(v)", produced by the machine learning component throughout the iterations in response to the training input data v. "M" designates the chosen model, such as MLC1, MLC2 as discussed above, or any other suitable learning model, fully connected NNs, CNNs, a mix of CNNs and NNs, SVMs or other. $f^L$ may be formulated in terms of a measure µ (·) of "closeness" to quantify the error Δ. Formally, $f^L$ may hence be written as:

$$f^L(v, v' \mid NP) = \mu(M(v) - v') \xrightarrow[NP]{} \Delta \qquad (1)$$

with Δ the error (a positive number), and µ (·) a suitable closeness measure, given the current set of model parameters NP. Measures µ envisaged herein include a Euclidean square distance, $(M(v)-v')^2$, to implement a least squares approach. Any suitable $L^p$ norms, with p other than ½ are also envisaged in embodiments.

In embodiments of the context finder MLC1, the following root mean squared error loss function can be used for training:

$$f^L = \text{Loss}_{RMSE} = \sqrt{\Sigma_i w_i (M(v_i) - v_i')^2} \qquad (2)$$

where $M(v_i)$ is the i-th target obtained by applying the context finder, given a current set of model parameters NP, to the i-th item $v_i$ of training input data, representing the predicted ROI coordinates and/or bolus tracking parameters BTM, $w_i$ is an optional scaling factor to account for possibly different ranges of the various output parameters, and $v_i'$ is the i-th target from the training data.

In embodiments of the bolus tracker, the loss function may be based on the Kullback-Leibler divergence (KBD) for µ. Specifically, a binary cross entropy loss function may be used for training. In a discrete setting as primarily envisaged herein, the KBD reduces to the following formulation of the binary cross entropy loss function:

$$f^L = \text{Loss}_{bce} = \Sigma_i - y_i \log(p_i) + (1-y_i)\log(1-p_i) \qquad (3)$$

where $v' = y_i$ is the i-th target, in this case the reference decision whether to trigger the diagnostic imaging (e.g., a full scan) or not, and $p_i = M(v)$ is the i-th output trigger schedule in terms of probability as output by the network MLC2 (given a current set of model parameters) in response to the i-th training input v comprising training (one or more) monitoring image (of projection or image domain).

It will be understood that the loss functions (2), (3) are exemplary embodiments and other type of formulations are also envisaged. Furthermore, the cross entropy setup (3) may be used in addition or instead for training the context finder MLC1 and the least square approach in (2) may be used in addition or instead for training the bolus tracker MLC2.

Given the loss function, the optimization, in particular the minimization problem may be formulated as finding the model parameters NP that reduce the loss function to a minimum (locally or globally):

$$\text{argmin}_{NP} f^L(v, v' \mid NP) \qquad (4)$$

Alternatively, (4) may be merely required to fall below a pre-defined acceptance threshold $f^L < \text{Th}$.

The optimization (4) may be subjected to regularization to enforce certain desirable properties of the model parameter solutions to be found in the parameter space. The regularization may be implemented by functional constraints to be taken into account when solving (4). In embodiments, the regularization may be enforced by sparsity constraints for instance. In addition or instead to explicit regularization, other, implicit regularization setups, may be implemented by including into the model one or more drop-out layers such as in CNN modelling. The drop-out layers, at random or in deterministic fashion, sever connections between nodes in different layers to so steer the optimization algorithm during execution to simpler solutions so as to combat overfitting phenomena.

If the machine learning component is an artificial neural-network, such as a fully connected network or a convolutional network, or a combination thereof, either of the recurrent or of the feed forward type, gradient descent type optimizations may be used to solve (4), which include in one embodiment the back propagation algorithm.

When the optimizations algorithm executes, the (current) model parameters are adjusted incrementally so as to minimize the loss function and this adjustment is repeated over a number of iteration cycles for a given training data item i. There is a second iteration where one iterates over the different items of training data input. In this manner, a double loop is implemented. It will be appreciated that the accumulated contributions that the loss function measures the accumulated contributions of all errors incurred by preferably all items in the training data set.

In one embodiment where the back propagation is used. In this embodiment, the training data is applied to the NN model having current model parameters. The training input data is forward-propagated therethrough to obtain the training output data as final output. The loss or deviation between target and training output is expressed in terms of error contributions for the individual neuronal nodes in the network. These error contributions are established in a back propagation step, where the overall error as measured by the loss function is distributed across the neutrons in dependence on their contribution to the errors. The contribution is measured by the current weights of their connections. The error contributions are then used in a gradient descent step to improve the loss function by adjusting, in an update step, the current new network parameters. The so updated model parameters are then to be used for the same data set in a next iterative step by forward propagating the training data through the (now updated) network, and so forth.

Although the learning of network like machine learning components such as artificial neural-networks CNN's rely on the described descent based optimization schemes such as the back propagation, other alternative optimization schemes may also be used in benefit. These alternatives include, for instance, the conjugal gradient descent methods, stochastic gradient descent methods, the BFGS method, the Nelder-Mead method, Newton-Raphson algorithms and others. That is not to say however that a gradient based method is necessarily required in all embodiments. It is not, for other optimization schemes, statistical, random or otherwise, may also be used in other embodiments, particularly in embodiments where the machine learning component to be trained has no network-like structure. Alternatives to non-network-like machine learning components envisaged herein includes the above mentioned support vector machines, decision trees, regression methods, all envisaged herein in alternative embodiments.

Although an artificial neural structure, such as the convolutional neural network structure or others such as fully connected ones, is mainly envisaged herein, this is not at the exclusion of other network like machine learning setups, such as (deep) belief networks, Boltzmann machines, but also Markov models, random fields and other graphical models. Common to at least this class of machine algorithms is that they are composed of a number of processing nodes, each capable of producing input and output, which they receive from or pass onto other nodes to which they connect.

As mentioned earlier the proposed system have been observed to yield good results if a deep learning architecture is used. The concept of deep learning is applicable not only to neural-networks but to other alternative network type machine learning architectures. In a feed forward artificial neural-network as discussed above, the depth corresponds to the number of hidden layers between the input and output layer. However, in other networks this correspondence may not be necessarily so. A general concept of network depth can be defined in terms of causal paths through the network that links a given final output to an initial input. The path describes all the processing nodes that contributed to the observed output. A length for these paths can be defined by the number of nodes through which the path passes. It can thus be assumed for instance that a recurrent network, may in fact be deeper than a feed forward network with more hidden layers. This is because in the recurrent network the depth is defined by the number of times the path transverses the network structure to produce the output and not only by the number of hidden layers. In other words, the recurring network with fewer hidden layers may be deeper than a feed forward network with more hidden layers. The depth is measured as the maximum causal path length ("PL_max") for instance, or in any other metric in terms of path length.

A depth (as measured in a suitable causal path length such as PL_max) of two has been found to yield good results but other, deeper architectures, such as any one of 3, 4, 5, 6, 7, 8, 9 or 10 or more than 10 are also envisaged herein. In some embodiments, the depth is in the tens or in the hundreds, although the depth must be traded off against the responsiveness when deployed and during learning. CNNs with depths of around 10 have been found to yield, for present purposes, accurate results with quick turnaround during deployment, with next to quasi-real-time performance. Depending or the hardware and load, a performance in the order of milliseconds may be achieved during deployment, in particular in forward-propagation through a neural network structure.

The above formulation of the training data in terms of pairs of input v and target v' may imply supervise learning approaches. However, there is no explicit labeling required. Instead, running a suitable search in a medical database using suitable data grabber as described above is all that it takes to perform the training of the proposed learning system. One may hence refer to the proposed system as an instance of unsupervised learning. Explicit labeling such as in image recognition task for autonomous driving, for instance, is not required herein which allows achieving high throughput and quick training of the MLC2, MLC1. Reinforced learning schemes and/or various hybrid approaches may also be considered in embodiments.

The network setups as discussed above at FIGS. 3,5 can be seen to be of hybrid character as they include portions that are fully connected and CNN portions that are not fully connected. Other such hybrid networks with fully and not-fully connected sub-networks are also envisaged. The nodes of pure or hybrid networks may be implemented in software as subroutines to implement their activation function. Alternatively, each or some nodes may be formulated in hardware each as a separate computing unit. The network may be operated as a distributed computational network, either during deployment or training. The computational burden is shared across a network of interconnected computing units. (Federated) Cloud architecture may be used with benefit in these types of embodiments. This distributed approach may be used with benefit for hybrid networks, with fully connected and CNN-type subnetworks, where the sub-networks are implemented by different computing units (e.g., servers) in the Cloud, possibly remote to each other, but communicatively coupled to provide or receive input or output, respectively, among and from each other. Central processing on a central server is also envisaged in alternative embodiments.

It will be understood that the ML components MLC1 and/or MLC2 and/or its training, may be implemented suitably by processing units PU such as GPU or others. GPU's (graphical processing unit) or TPU's (tensor processing units) are optimized to perform tensor or matrix operations (which are series of dot products). It has been found that tensor or matrix operations can be used with benefit for training or deployment. GPUs, TPUs or similar microprocessors are in general optimized for parallel computing, such as in multi-core systems.

Suitable circuitry to implement the above described systems SSI in software arranged on a computing device such as a stationary computer, a workstation, for instance a laptop, handheld device, tablet or others.

The proposed deployment and/or training may also be implemented in a client-server based environment. In particular, the training or deployment may be performed by one or more servers in a cloud based architecture.

In addition to software based circuitry the systems for deployment or training as described above may also be implemented as hard coded micro-chips. Specific circuitry such as application specific integrated circuitry ASICS Circuitry may be used. A system-on-a-chip (SOC) may include discrete and/or integrated circuitry, and combinations thereof. In an alternative embodiment, the circuitry may include suitably configured field-programmable gate array FGPA's. In particular, the described imaging support system SSI may be integrated at least in part into the controller CC of the imaging apparatus or maybe otherwise integrated into the imaging apparatus. The system SSI may be integrated into a work-station or other computer unit associated with the imaging apparatus.

The trained MLC may be held in a central memory MEM or may be distributed in a plurality of servers or memory devices preferably connectable to an end user computing device (laptops, smart phone, desktop computer, etc.) to request execution of the training and/or deployment according to any one of the above described systems.

Training and deployment may be run on the hardware equipment, or may be run on different computing hardware. Preferably, the hardware for the training is configured for higher performance than for deployment as training may be computational more demanding. Although training may be a one-off operation initially, it may be repeated with new training data. The machine learning components MLC1, MLC2 may be switchable into training or deployment mode.

In another exemplary embodiment of the present invention, a computer program or a computer program element is provided that is characterized by being adapted to execute the method steps of the methods according to any one of the preceding embodiments, on an appropriate computerized system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (transitory or non-transitory), such as an optical storage medium or a solid-state medium supplied together with or as part of other hardware, but may also be distributed in other forms, such as via the internet or other wired or wireless (tele-)communication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A system for image processing, comprising:
one or more receivers configured to receive input data including a non-diagnostic X-ray image, procured through an X-ray imaging apparatus configured for spectral imaging, of a target location in a conduit of an object, the conduit including a target substance, the target substance propagatable in the conduit towards the target location;
one or more processors configured to process, with a pre-trained-machine learning algorithm, the non-diagnostic X-ray image to obtain output data indicative of an arrival of the target substance at the target location; and
an output configured to output the output data, wherein the one or more processors are further configured to trigger an acquisition of a diagnostic X-ray image in response to the output data, and wherein the diagnostic X-ray image has a higher radiation dose than the non-diagnostic X-ray image.

2. The system of claim 1, wherein the one or more processors are further configured to control operation of the X-ray imaging apparatus based on the output data.

3. The system of claim 1, wherein the image acquisition operation is triggered to include acquiring a plurality of projection images from different directions relative to the target location.

4. The system of claim 1, wherein the X-ray image is processed by a neural network.

5. The system of claim 4, wherein the neural network includes at least two hidden layers, wherein at least one hidden layer causes a reduction of data dimension and the at least one other hidden layer of the at least two layers causes an increase in data dimension.

6. The system of claim 1, wherein i) the conduit includes at least a part of a human or animal vessel holding or conveying body fluid and/or ii) wherein the target substance includes contrast agent for medical imaging.

7. The system of claim 1, wherein the input data includes at least one of i) data that describes the object, and ii) data that describe a manner of propagation of the substance.

8. A computer implemented method of supporting an imaging operation, comprising:
receiving input data including a non-diagnostic X-ray image, procured through an X-ray imaging apparatus configured for spectral imaging, of a target location in a conduit of an object, the conduit including a target substance, the target substance propagatable in the conduit towards the target location;

processing, by one or more processors with a pre-trained-machine learning algorithm, the non-diagnostic X-ray image to obtain output data indicative of an arrival of the target substance at the target location; and outputting the output data, wherein the one or more processors are further configured to trigger an acquisition of a diagnostic X-ray image in response to the output data, and wherein the diagnostic X-ray image has a higher radiation dose than the non-diagnostic X-ray image.

9. A non-transitory computer readable medium for storing executable instructions, which cause a method to be performed according to claim 8.

* * * * *